United States Patent
Furuya et al.

(10) Patent No.: US 12,379,367 B2
(45) Date of Patent: *Aug. 5, 2025

(54) METHOD FOR SETTING POLYMERIZATION CONDITION AND METHOD FOR MANUFACTURING OPTICAL MATERIAL

(71) Applicant: MITSUI CHEMICALS, INC., Tokyo (JP)

(72) Inventors: Masayuki Furuya, Arao (JP); Takeshi Nishimura, Yanagawa (JP)

(73) Assignee: MITSUI CHEMICALS, INC., Tokyo (JP)

( * ) Notice: Subject to any disclaimer, the term of this patent is extended or adjusted under 35 U.S.C. 154(b) by 1233 days.

This patent is subject to a terminal disclaimer.

(21) Appl. No.: 17/262,265

(22) PCT Filed: Jul. 24, 2019

(86) PCT No.: PCT/JP2019/028968
§ 371 (c)(1),
(2) Date: Jan. 22, 2021

(87) PCT Pub. No.: WO2020/022369
PCT Pub. Date: Jan. 30, 2020

(65) Prior Publication Data
US 2021/0372984 A1    Dec. 2, 2021

(30) Foreign Application Priority Data

Jul. 24, 2018   (JP) .................................. 2018-138123

(51) Int. Cl.
*G01N 33/44*   (2006.01)
*B29D 11/00*   (2006.01)
(Continued)

(52) U.S. Cl.
CPC .......... *G01N 33/442* (2013.01); *B29D 11/00* (2013.01); *C08G 75/08* (2013.01); *G02B 1/04* (2013.01)

(58) Field of Classification Search
None
See application file for complete search history.

(56) References Cited

U.S. PATENT DOCUMENTS 6,365,707 B1    4/2002 Ryu et al.
9,182,520 B2    11/2015 Okada et al.
(Continued)

FOREIGN PATENT DOCUMENTS

EP    3135710 A1    3/2017
JP    2001106703 A    4/2001
(Continued)

OTHER PUBLICATIONS

International Search Report (PCT/ISA/210) issued on Sep. 24, 2019, by the Japan Patent Office as the International Searching Authority for International Application No. PCT/JP2019/028968.
(Continued)

*Primary Examiner* — Tae H Yoon
(74) *Attorney, Agent, or Firm* — BUCHANAN INGERSOLL & ROONEY PC

(57) ABSTRACT

The method for setting polymerization conditions includes a physical property acquiring step, in which, when a composition which includes a polymerizable reactive compound including an episulfide compound, and a polymerization catalyst is heated and maintained at a predetermined temperature, a physical property value a derived from a functional group of the polymerizable reactive compound before heating and a physical property value b derived from a remaining functional group after maintaining heat for a predetermined time, are acquired; a remaining functional
(Continued)

group ratio calculating step of calculating a remaining functional group ratio; a reaction rate coefficient calculating step for calculating a reaction rate coefficient; and a polymerization temperature calculating step of back-calculating each polymerization temperature every predetermined time in a polymerization time.

15 Claims, 8 Drawing Sheets

(51) Int. Cl.
  *C08G 75/08* (2006.01)
  *G02B 1/04* (2006.01)

(56) References Cited

U.S. PATENT DOCUMENTS

| | | |
|---|---|---|
| 9,447,226 B2 | 9/2016 | Okada et al. |
| 9,529,117 B2 | 12/2016 | Kamura et al. |
| 2004/0178526 A1 | 9/2004 | Kojima et al. |
| 2012/0123081 A1 | 5/2012 | Okada et al. |
| 2014/0357835 A1 | 12/2014 | Kamura et al. |
| 2015/0166720 A1 | 6/2015 | Okada et al. |
| 2017/0212054 A1 | 7/2017 | Reed et al. |

FOREIGN PATENT DOCUMENTS

| | | | |
|---|---|---|---|
| JP | 2001220444 A | | 8/2001 |
| JP | 2003252910 A | | 9/2003 |
| JP | 2004091688 A | | 3/2004 |
| JP | 2004209968 A | | 7/2004 |
| JP | 2005350531 A | | 12/2005 |
| JP | 2007238952 A | | 9/2007 |
| JP | 2009226742 A | | 10/2009 |
| JP | 2010105229 A | | 5/2010 |
| JP | 2012240414 A | | 12/2012 |
| JP | 2014047334 A | | 3/2014 |
| JP | 2017531076 A | | 10/2017 |
| JP | 6564950 B1 | * | 8/2019 |
| WO | 2011007749 A1 | | 1/2011 |
| WO | WO 2012144594 A1 | * | 10/2012 |
| WO | 2013122068 A1 | | 8/2013 |
| WO | 2014038654 A1 | | 3/2014 |

OTHER PUBLICATIONS

Written Opinion (PCT/ISA/237) issued on Sep. 24, 2019, by the Japan Patent Office as the International Searching Authority for International Application No. PCT/JP2019/028968.

* cited by examiner

METHOD FOR SETTING POLYMERIZATION CONDITION AND METHOD FOR MANUFACTURING OPTICAL MATERIAL

CROSS-REFERENCE TO RELATED APPLICATIONS

This application is a U.S. National Stage Application of PCT/JP2019/028968, filed Jul. 24, 2019, which claims priority to Japanese Patent Application No. 2018-138123, filed Jul. 24, 2018, the entire contents of all of which are hereby incorporated by reference.

TECHNICAL FIELD

The present invention relates to a method for setting polymerization condition and a method for manufacturing an optical material having an excellent appearance.

BACKGROUND ART

Plastic lenses are lighter and harder to break than inorganic lenses and are able to be dyed and have thus rapidly become widespread as optical materials for spectacle lenses and camera lenses and the like. So far, various molded articles for lenses have been developed and used.

There is a demand for higher performance for plastic lens resins and there is a demand for a higher refractive index, a higher Abbe number, a lower specific gravity, a higher heat resistance, and the like. Various resin materials for lenses have been developed and used so far.

Among these, an optical material formed of a sulfide-based resin has a high refractive index and a high Abbe number and is being studied as an ultrahigh refractive index material having a refractive index of more than 1.6. The sulfide-based resin is obtained by polymerizing a polymerizable composition including an episulfide compound.

Patent Document 1 describes a method for manufacturing a plastic lens including an injection step of adjusting a polymerizable composition containing an episulfide compound to a predetermined temperature or lower and filling the composition into a mold, and a curing step of exposing the mold under predetermined temperature/time conditions to polymerize the polymerizable composition.

Patent Document 2 proposes a method for manufacturing a plastic lens obtained by casting polymerization of a mixture containing an episulfide compound, in which a preliminary reaction is carried out until each component enters a state in which precipitation due to recrystallization does not occur even when cooled, and then an internal mold release agent is added thereto.

Patent Documents 3 and 4 propose a method for manufacturing a polymerizable composition for an optical material in which a pre-reaction liquid is obtained by carrying out a pre-reaction on a mixture containing an episulfide compound at a predetermined reaction temperature, and a polymerization catalyst is added to the pre-reaction liquid and reacted at a predetermined temperature/time.

Patent Document 5 proposes, as a method for manufacturing a thick plastic lens having a high refractive index, a manufacturing method provided with a holding step of filling a polymerizable composition into a mold and then maintaining the polymerizable composition at an initial temperature of the time of the filling or higher, and a cooling step of cooling the polymerizable composition. As the resin obtained from the composition, an episulfide resin is exemplified.

Patent Document 6 discloses a method for manufacturing a plastic lens having a curing step provided with a holding step of maintaining, after a filling step, a polymerizable composition at the initial temperature of the time of the filling step or higher, and a cooling step of cooling the polymerizable composition after the holding step. An episulfide compound is exemplified as the compound included in the composition.

Patent Document 7 discloses a multi-component copolymerization reaction simulation program and a multi-component copolymerization reaction calculation method for simulating a multi-component type radical polymerization reaction.

Patent Document 8 discloses a method for simulating a radical polymerization reaction or emulsion polymerization to determine polymer manufacturing conditions.

Patent Document 9 discloses a process control system for performing a polymerization reaction in a batch reaction tank.

RELATED DOCUMENT

Patent Document

[Patent Document 1] Japanese Unexamined Patent Publication No. 2004-209968
[Patent Document 2] Japanese Unexamined Patent Publication No. 2010-105229
[Patent Document 3] Japanese Unexamined Patent Publication No. 2014-47334
[Patent Document 4] International Publication No. 2013/122068
[Patent Document 5] Japanese Unexamined Patent Publication No. 2012-240414
[Patent Document 6] Japanese Unexamined Patent Publication No. 2009-226742
[Patent Document 7] Japanese Unexamined Patent Publication No. 2004-091688
[Patent Document 8] Japanese Unexamined Patent Publication No. 2003-252910
[Patent Document 9] Japanese Unexamined Patent Publication No. 2001-106703

SUMMARY OF THE INVENTION

Technical Problem

As disclosed in Patent Documents 1 to 6, a plastic lens is usually formed by polymerizing and curing a polymerizable composition filled in a pair of molds; however, the polymerization rate of the polymerizable composition changes depending on the temperature and a slight temperature distribution locally increases or decreases the polymerization rate.

For this reason, for example, a portion where the polymerization rate is increased has a higher molecular weight than others and precipitates downward or rises upward. In addition, in the molds, convection currents may also be generated in the polymerizable composition. When the polymerizable composition is cured while traces thereof remain, there is a concern that optical distortion or striae may be generated in the plastic lens.

In particular, a compound having an episulfide group has high reactivity, and in a case where a polymerizable composition including such a compound is used to manufacture an optical material, excessive polymerization or a side reaction proceeds and it is difficult to manufacture a lens with reduced striae.

The polymerization temperature conditions are extremely important conditions for suppressing optical distortion and striae. Examples of the polymerization temperature conditions include the conditions disclosed in Patent Documents 1 to 4; however, a predetermined temperature range is set simply based on experience.

Patent Documents 5 and 6 describe the problem that, when a local increase/decrease in the polymerization rate is generated, optical distortion and striae are generated in the plastic lens. As clear from the use of the term "increase/decrease", deviation from the standard polymerization rate is the problem. The "increase/decrease" of the polymerization rate in these cited documents means a deviation when the polymerization process in which optical distortion or striae are not generated is taken as a reference. In Patent Documents 5 and 6, in order to suppress such a deviation, in the curing step of the polymerizable composition, temperature increases, temperature maintenance, and temperature decreases are appropriately combined based on experience.

These patent documents do not disclose the idea of controlling, at every time, the polymerization rate at each time from the start of polymerization up to a predetermined time.

Patent Documents 7 to 9 disclose simulations of the polymerization reaction in the polymerization process, and, in Patent Document 7, the calculation of the polymerization ratio is performed at a plurality of times (paragraphs 0021 to 0022, FIG. 8, and the like).

However, in the calculations in these patent documents, the polymerization ratio and the like are calculated with the temperature as a given condition. That is, in the calculations in these patent documents, the temperature is used as a "condition necessary for the calculation".

Setting the temperature conditions according to theoretical analysis of the reaction rate of the polymerizable composition as above has not yet been performed.

An object of the present invention is to set a polymerization temperature condition under which optical distortion or striae accompanying curing of a polymerizable composition including an episulfide compound is suppressed and an optical material having an excellent appearance is obtained.

Solution to Problem

As a result of intensive studies conducted by the present inventors, it was found that, in a case of using an episulfide compound, appropriately setting polymerization temperature conditions according to a predetermined analysis makes it possible to increase the polymerization ratio of the optical material and to further suppress variations in a polymerization rate in the process of polymerizing and curing the optical material and, as a result, the generation of optical distortion and striae is suppressed and it is possible to obtain an optical material having an excellent appearance, thereby completing the present invention.

That is, it is possible to illustrate the present invention as follows.

[1] A method for setting polymerization condition, including a physical property acquiring step of, when a composition which includes a polymerizable reactive compound including an episulfide compound, and a polymerization catalyst is heated and maintained at a predetermined temperature, acquiring a physical property value a derived from a functional group of the polymerizable reactive compound before heating and a physical property value b derived from a remaining functional group after maintaining heat for a predetermined time, a remaining functional group ratio calculating step of calculating a remaining functional group ratio from the physical property value a and the physical property value b, a reaction rate coefficient calculating step of calculating a reaction rate coefficient from the remaining functional group ratio based on a reaction rate equation, and a polymerization temperature calculating step of back-calculating each polymerization temperature every predetermined time in a polymerization time based on the reaction rate equation, using the reaction rate coefficient, such that the following conditions are satisfied (Conditions)

in a range where the polymerization ratio is 0% or more and 20% or less, a polymerization rate is more than 0%/hr and 3.0%/hr or less and a standard deviation is 0.8%/hr or less.

[2] The method for setting polymerization condition according to [1], in which the episulfide compound is represented by General Formula (1),

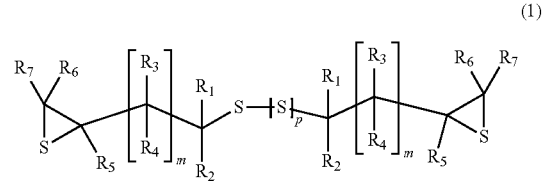

in which in General Formula (1), $R_1$ to $R_7$ may be the same or different and represent a hydrogen atom, a linear or branched alkyl group having 1 or more and 10 or less carbon atoms, or a substituted or unsubstituted aryl group having 6 or more and 18 or less carbon atoms. m represents an integer of 0 or more and 2 or less. p represents an integer of 0 or more and 4 or less.

[3] The method for setting polymerization condition according to [1] or [2], in which a molar ratio of the functional group of the episulfide compound is 60 or more with respect to 100 by mole of a total of the functional group moles of the polymerizable reactive compound.

[4] The method for setting polymerization condition according to anyone of [1] to [3], in which the polymerizable reactive compound includes at least one type selected from an active hydrogen compound, a polyiso(thio)cyanate compound, and an epoxy compound.

[5] The method for setting polymerization condition according to any one of [1] to [4], in which the physical property value a and the physical property value b are a heat value, a specific gravity, a weight average molecular weight, a number average molecular weight, a $^1$H-NMR spectral intensity, or a $^{13}$C-NMR spectral intensity.

[6] The method for setting polymerization condition according to [1], further including a polymerization time setting step of selecting a reaction time, during which the polymerization ratio increases from more than 20% up to 90%, from 0.1 to 150 hours, after the polymerization temperature calculating step.

[7] A method for manufacturing an optical material including a step of calculating polymerization temperature conditions every predetermined time in a polymerization time by the following step (A), a step of injecting a composition which includes a polymerizable reactive compound including an episulfide compound, and a polymerization catalyst into a mold, and a step of polymerizing and curing the composition such that the calculated polymerization temperature conditions for each polymerization time are satisfied step (A):

a physical property acquiring step of, when the composition is heated and maintained at a predetermined temperature, acquiring a physical property value a derived from a functional group of the polymerizable reactive compound included in the composition before heating and a physical property value b derived from a remaining functional group after maintaining heat for a predetermined time, a remaining functional group ratio calculating step of calculating a remaining functional group ratio from the physical property value a and the physical property value b, a reaction rate coefficient calculating step of calculating a reaction rate coefficient from the remaining functional group ratio based on a reaction rate equation; and a polymerization temperature calculating step of back-calculating each polymerization temperature every predetermined time in a polymerization time based on the reaction rate equation, using the reaction rate coefficient, such that the following conditions are satisfied (Conditions)

in a range where the polymerization ratio is 0% or more and 20% or less, a polymerization rate is more than 0%/hr and 3.0%/hr or less and a standard deviation is 0.8%/hr or less.

[8] The method for manufacturing the optical material according to [7], in which the polymerization is performed under polymerization temperature conditions obtained by the method according to any one of [1] to [4].

[9] The method for manufacturing an optical material according to [7] or [8], in which the episulfide compound is represented by General Formula (1),

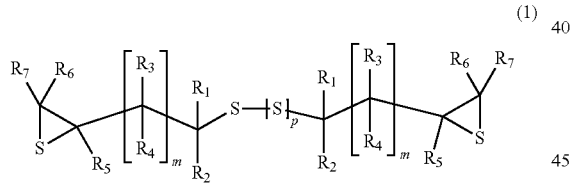

in which in General Formula (1), $R_1$ to $R_7$ may be the same or different and represents a hydrogen atom, a linear or branched alkyl group having 1 or more and 10 or less carbon atoms, or a substituted or unsubstituted aryl group having 6 or more and 18 or less carbon atoms. m represents an integer of 0 or more and 2 or less. p represents an integer of 0 or more and 4 or less.

[10] The method for manufacturing an optical material according to any one of [7] to [9], in which a molar ratio of the functional group of the episulfide compound is 60 or more with respect to 100 by mole of a total of the functional group moles of the polymerizable reactive compound.

[11] The method for manufacturing an optical material according to anyone of [7] to [10], in which the polymerizable reactive compound includes at least one type selected from an active hydrogen compound and an epoxy compound.

[12] The method for manufacturing an optical material according to [7], further including a polymerization time setting step of selecting a reaction time, during which the polymerization ratio increases from more than 20% up to 90%, from 0.1 to 150 hours, after the polymerization temperature calculating step.

[13] A polymerization condition setting device including a physical property acquisition unit which, when a composition which includes a polymerizable reactive compound including an episulfide compound, and a polymerization catalyst is heated and maintained at a predetermined temperature, acquires a physical property value a derived from a functional group of the polymerizable reactive compound before heating and a physical property value b derived from a remaining functional group after maintaining heat for a predetermined time, a remaining functional group ratio calculating unit for calculating a remaining functional group ratio from the physical property value a and the physical property value b, a reaction rate coefficient calculating unit for calculating a reaction rate coefficient from the remaining functional group ratio based on the reaction rate equation, and a polymerization temperature calculating unit for back-calculating each polymerization temperature every predetermined time in a polymerization time based on the reaction rate equation, using the reaction rate coefficient, such that the following conditions are satisfied (Conditions)

in a range where the polymerization ratio is 0% or more and 20% or less, the polymerization rate is more than 0%/hr and 3.0%/hr or less, and the standard deviation is 0.8%/hr or less.

[14] A computer program for setting polymerization conditions for a composition which includes a polymerizable reactive compound including an episulfide compound, and a polymerization catalyst, in which the computer programs causes a computer to function as:

a physical property acquisition unit which, when a composition which includes a polymerizable reactive compound including an episulfide compound, and a polymerization catalyst is heated and maintained at a predetermined temperature, acquires a physical property value a derived from a functional group of the polymerizable reactive compound before heating and a physical property value b derived from a remaining functional group after maintaining heat for a predetermined time, a remaining functional group ratio calculation unit for calculating the remaining functional group ratio from the physical property value a and the physical property value b, a reaction rate coefficient calculation unit for calculating a reaction rate coefficient from the remaining functional group ratio based on a reaction rate equation, and a polymerization temperature calculation unit for back-calculating each polymerization temperature every predetermined time in a polymerization time based on the reaction rate equation, using the reaction rate coefficient, such that the following conditions are satisfied (Conditions)

in a range where the polymerization ratio is 0% or more and 20% or less, the polymerization rate is more than 0%/hr and 3.0%/hr or less, and the standard deviation is 0.8%/hr or less.

[15] An optical material manufacturing device including a heating unit for heating a composition which includes a polymerizable reactive compound including an episulfide compound, and a polymerization catalyst, the polymerization condition setting device according to [13], and a control unit for controlling the heating unit to heat the composition including the polymerizable reactive compound, which includes the episulfide compound, and the polymerization catalyst, based on polymerization temperature conditions obtained by the polymerization condition setting device.

In the present invention, the polymerization ratio [%] is a ratio of the polymerizable reactive compound which is polymerized, in the used polymerizable reactive compounds including an episulfide compound. A polymerization ratio of 0% means a state in which the polymerization of the polymerizable reactive compound has not started and the polymerization starts from the point when the polymerization catalyst is added thereto and mixed therein. The polymerization rate [%/h] is a value obtained by dividing the polymerization ratio by time. The polymerization time is the time from when the polymerizable reactive compound, which includes an episulfide compound, and the polymerization catalyst are added and mixed until a predetermined polymerization ratio is reached.

Advantageous Effects of Invention

According to the method for setting polymerization condition of the present invention, it is possible to obtain polymerization temperature conditions under which the generation of optical distortion and striae is suppressed and to obtain an optical material having an excellent appearance. Furthermore, the method for manufacturing an optical material using the obtained polymerization temperature conditions makes it possible to obtain an optical material in which the generation of optical distortion and striae is suppressed and which has an excellent appearance. In particular, even in an optical material such as a lens having a large layer thickness in which optical distortion and striae are easily generated, it is possible to effectively suppress the generation of optical distortion and striae.

Moreover, according to the present invention, it is also possible to provide a polymerization condition setting device, a computer program for calculating polymerization temperature conditions, and an optical material manufacturing device provided with the polymerization condition setting device.

BRIEF DESCRIPTION OF THE DRAWINGS

The above and other objects, features and advantages will become more apparent from preferable embodiments described below and the accompanying drawings below.

DESCRIPTION OF EMBODIMENTS

Figure 1:
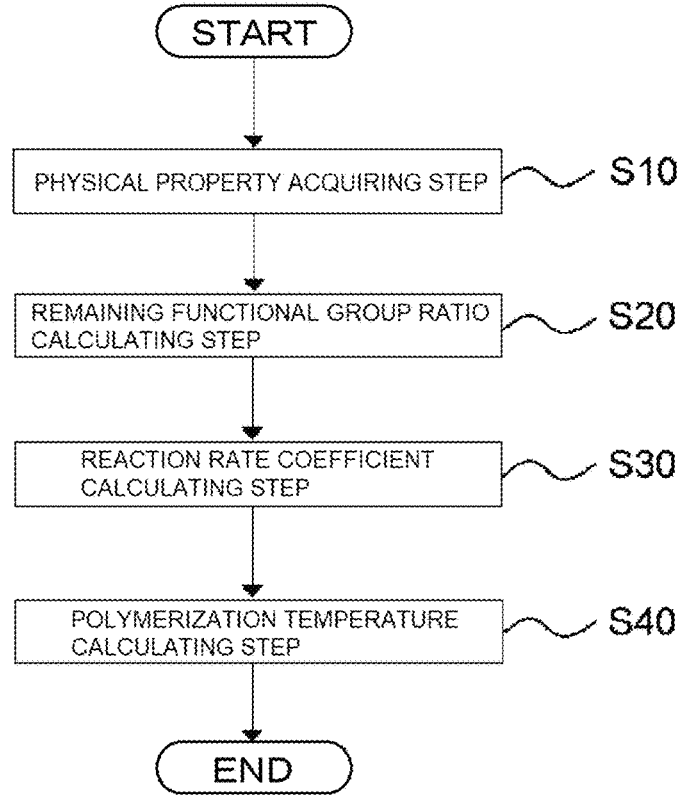
FIG. 1 is a flowchart of a method for setting polymerization condition according to the present embodiment.

First, a description will be given of the method for setting polymerization condition (simulation) and standard deviation in the present invention.
(1) Method for Setting Polymerization Condition (Simulation)

Simulations of chemical reactions are usually calculated by computers in the form of sequential calculations. When calculating how the polymerization ratio increases over time in the polymerization reaction (in other words, how the concentration of the polymerizable remaining functional groups decreases), calculations are carried out sequentially at each time. That is, after the initial conditions of the temperature and the concentration of the polymerizable functional group are given, the calculation of determining the concentration of the polymerizable functional group at the next time (t+Δt) is repeated based on the temperature and the concentration of the polymerizable functional group at the time t (such calculations are referred to below as "sequential calculations").

The sequential calculations are also the basis for the simulation in the present invention. That is, in the present invention, as in the related art techniques in the cited documents 7 to 9 and the like, the state in the polymerization system at the next time (t+Δt) is predicted based on the temperature and the concentration of the polymerizable remaining functional group at the time t.

The difference to the related art techniques in the cited documents 7 to 9 and the like is the point that the target to be calculated at the next time (t+Δt) is not the concentration of the polymerizable remaining functional group but the reaction rate coefficient.

The object and the target of calculation are different between the present invention and the related art techniques. In the calculation in the related art techniques, the temperature is used as the "condition necessary for the calculation", whereas in the present invention, the temperature is the target to be calculated and is the "calculation result". In the present invention, the temperature transition is calculated such that the desired polymerization transition is obtained.

In the simulation of the present invention, in the time section from time t to immediately before the next time (t+Δt) (the region where the time value is t or more and less than t+Δt), the reaction rate (polymerization rate) is set to v which is initially set, then, the reaction rate coefficient at the next time (t+Δt) is determined so as to satisfy the condition that the reaction rate at the next time (t+Δt) is also equal to v.

When calculating how the polymerization ratio increases over time in the polymerization reaction (in other words, how the concentration of the polymerizable remaining functional group decreases), calculations are carried out sequentially at each time.

In the simulation of the present embodiment, the reaction temperature is calculated by calculating the reaction rate coefficient at the next time (t+Δt) based on the temperature and the concentration of the polymerizable remaining functional group at the time t. In the present embodiment, the temperature is the target to be calculated and it is possible to determine the temperature transition by calculation so as to obtain the desired polymerization transition.

In the present invention, in the time section from time t to immediately before the next time (t+Δt) (the region where the time value is t or more and less than t+Δt), the reaction rate (polymerization rate) is set to v which is initially set, then, the reaction rate coefficient at the next time (t+Δt) is determined so as to satisfy the condition that the reaction rate at the next time (t+Δt) is also equal to v.

(2) Standard Deviation

According to the present invention, the "standard deviation" does not become zero even though it is the result of a simulation in which calculation is performed at predetermined time intervals. A description will be given below of the reason for this by taking the primary reaction of the episulfide compound, which is a polymerizable reactive compound, as an example.

In the present invention, the polymerization ratio transition from the initial polymerization to a polymerization ratio of 20% is a linear transition. Therefore, as shown in the following graph in which the horizontal axis is time and the vertical axis is the polymerization ratio, the polymerization ratio transitions from $CV_1$ to $CV_2$ during a time $\Delta t$ when a time $t_0$ changes to a time $t_1$.

TABLE 1

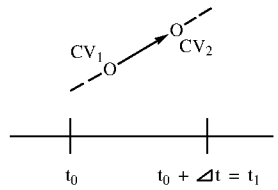

If $CV_2 - CV_1 = x$ (%), it is possible to represent x by Equation 1.

$$x = \int_{t_0}^{t_1} v \, dt \qquad \text{Equation 1}$$

v: reaction rate

Since v=k[A] (k: reaction rate coefficient, [A]: episulfide compound concentration), Equation 1 becomes Equation 2 below.

$$x = \int_{t_0}^{t_1} k[A] \, dt \qquad \text{Equation 2}$$

Here, since k is a function of temperature, k is expressed as k(T), and since [A] is a function of time, [A] is expressed as A(t), at which time, Equation 2 becomes Equation 3 below.

$$x = \int_{t_0}^{t_1} [k(T) \times A(t)] \, dt \qquad \text{Equation 3}$$

In order to know how much the reaction progresses over time Δt, in other words, what the value of x becomes, to be precise, it is necessary to carryout calculations based on the value of A(t), which changes over time.

However, in the simulation, the value of A(t) is assumed as follows from t0 to (t0+Δt).

$$K(T) = \text{const} = k(T)_{t=t0}$$

$$A(t) = \text{const} = [A]_{t=t0}$$

Accordingly, in the simulation, Equation 3 is calculated as Equation 3' as follows.

$$X = \int_{t_0}^{t_1} [k(T) \times A(t)] \, dt \qquad \text{Equation 3}$$

$$\approx k(T)_{t=t_0} \times [A]_{t=t_0} \times \Delta t \qquad \text{Equation 3'}$$

There is a difference between Equation 3 and Equation 3', and if the time Δt is made large, this difference becomes large. This is the reason why the "deviation" from the linear transition occurs.

In this manner, there will be a deviation between the target value and the simulation result. That is, there is a deviation between the target polymerization ratio determined based on the average polymerization rate and the polymerization ratio at each time determined as a result of the calculation. The standard deviation of the polymerization rate occurs due to the accumulation of the deviations at each time.

A description will be given below of embodiments of the present invention with reference to the drawings. In all the drawings, the same constituent components will be given the same reference numerals and description thereof will not be repeated.

In the below description, a storage unit 100, a physical property acquiring unit 120, a remaining functional group ratio calculating unit 140, a reaction rate coefficient calculating unit 160, and a polymerization temperature calculating unit 180 of a polymerization condition setting device 10 are shown as blocks of functional units rather than a configuration of hardware units. The storage unit 100, the physical property acquiring unit 120, the remaining functional group ratio calculating unit 140, the reaction rate coefficient calculating unit 160, and the polymerization temperature calculating unit 180 of the polymerization condition setting device 10 are implemented by any combination of hardware and software based on the CPU of any computer, a memory, a program for implementing the constituent components of figures loaded into a memory, a storage medium such as a hard disk for storing such a program, or a network connection interface. The implementation method and apparatus may have various modifications.

FIG. 1 is a flowchart of the method for setting polymerization condition according to the present embodiment.

The method for setting polymerization condition according to the present embodiment is a method for setting polymerization temperature conditions for a composition which includes a polymerizable reactive compound including an episulfide compound, and a polymerization catalyst.

As shown in FIG. 1, the method for setting polymerization condition includes a physical property acquiring step S10, a remaining functional group ratio calculating step S20, a reaction rate coefficient calculating step S30, and a polymerization temperature calculating step S40. In the physical property acquiring step S10, in a case of heating a composition which includes a polymerizable reactive compound including an episulfide compound, and a polymerization catalyst and maintaining a predetermined temperature, a physical property value a derived from a functional group of the polymerizable reactive compound before heating and a physical property value b derived from a remaining functional group after maintaining heat for a predetermined time are acquired. In the remaining functional group ratio calculating step S20, the remaining functional group ratio is calculated from the physical property value a and physical property value b. In the reaction rate coefficient calculating step S30, a reaction rate coefficient is calculated from the remaining functional group ratio based on a reaction rate equation. In the polymerization temperature calculating step S40, each polymerization temperature is back-calculated every predetermined time in a polymerization time based on the reaction rate equation, using the reaction rate coefficient, such that the following conditions are satisfied.

Conditions: In a range where the polymerization ratio is 0% or more and 20% or less, a polymerization rate is more than 0%/hr and 3.0%/hr or less and a standard deviation is 0.8%/hr or less.

A description will be given below of the polymerizable reactive compound which includes the episulfide compound, the polymerization catalyst, and the composition including the above, which are used in the present embodiment.

The episulfide compound in the present embodiment is a compound having one or more episulfide groups and is not particularly limited as long as it is possible to exhibit the effects of the present invention.

Examples of the episulfide compound include epithioethylthio compounds such as bis(1,2-epithioethyl)sulfide, bis(1,2-epithioethyl)disulfide, bis(epithioethylthio)methane, bis(epithioethylthio)benzene, bis[4-(epithioethylthio)phenyl]sulfide, and bis[4-(epithioethylthio)phenyl]methane; chained aliphatic 2,3-epithiopropylthio compounds such as bis(2,3-epithiopropyl)sulfide, bis(2,3-epithiopropyl)disulfide, bis(2,3-epithiopropylthio)methane, 1,2-bis(2,3-epithiopropylthio)ethane, 1,2-bis(2,3-epithiopropylthio)propane, 1,3-bis(2,3-epithiopropylthio)propane, 1,3-bis(2,3-epithiopropylthio)-2-methylpropane, 1,4-bis(2,3-epithiopropylthio)butane, 1,4-bis(2,3-epithiopropylthio)-2-methylbutane, 1,3-bis(2,3-epithiopropylthio)butane, 1,5-bis(2,3-epithiopropylthio)pentane, 1,5-bis(2,3-epithiopropylthio)-2-methylpentane, 1,5-bis(2,3-epithiopropylthio)-3-thiapentane, 1,6-bis(2,3-epithiopropylthio)hexane, 1,6-bis(2,3-epithiopropylthio)-2-methylhexane, 1,8-bis(2,3-epithiopropylthio)-3,6-dithiaoctane, 1,2,3-tris(2,3-epithiopropylthio)propane, 2,2-bis(2,3-epithiopropylthio)-1,3-bis(2,3-epithiopropylthiomethyl)propane, 2,2-bis(2,3-epithiopropylthiomethyl)-1-(2,3-epithiopropylthio)butane, 1,5-bis(2,3-epithiopropylthio)-2-(2,3-epithiopropylthiomethyl)-3-thiapentane, 1,5-bis(2,3-epithiopropylthio)-2,4-bis(2,3-epithiopropylthiomethyl)-3-thiapentane, 1-(2,3-epithiopropylthio)-2,2-bis(2,3-epithiopropylthiomethyl)-4-thiahexane, 1,5,6-tris(2,3-epithiopropylthio)-4-(2,3-epithiopropylthiomethyl-3-thiahexane, 1,8-bis(2,3-epithiopropylthio)-4-(2,3-epithiopropylthiomethyl)-3,6-dithiaoctane, 1,8-bis(2,3-epithiopropylthio)-4,5-bis(2,3-epithiopropylthiomethyl)-3,6-dithiaoctane, 1,8-bis(2,3-epithiopropylthio)-4,4-bis(2,3-epithiopropylthiomethyl)-3,6-dithiaoctane, 1,8-bis(2,3-epithiopropylthio)-2,5-bis(2,3-epithiopropylthiomethyl)-3,6-dithiaoctane, 1,8-bis(2,3-epithiopropylthio)-2,4,5-tris(2,3-epithiopropylthiomethyl)-3,6-dithiaoctane, 1,1,1-tris[[2-(2,3-epithiopropylthio)ethyl]thiomethyl]-2-(2,3-epithiopropylthio)ethane, 1,1,2,2-tetrakis[[2-(2,3-epithiopropylthio)ethyl]thiomethyl]ethane, 1,11-bis(2,3-epithiopropylthio)-4,8-bis(2,3-epithiopropylthiomethyl)-3,6,9-trithiaundecane, 1,11-bis(2,3-epithiopropylthio)-4,7-bis(2,3-epithiopropylthiomethyl)-3,6,9-trithiaundecane, and 1,11-bis(2,3-epithiopropylthio)-5,7-bis(2,3-epithiopropylthiomethyl)-3,6,9-trithioundecane; cycloaliphatic 2,3-epithiopropylthio compounds such as 1,3-bis(2,3-epithiopropylthio)cyclohexane, 1,4-bis(2,3-epithiopropylthio)cyclohexane, 1,3-bis(2,3-epithiopropylthiomethyl)cyclohexane, 1,4-bis(2,3-epithiopropylthiomethyl)cyclohexane, 2,5-bis(2,3-epithiopropylthiomethyl)-1,4-dithiane, 2,5-bis[[2-(2,3-epithiopropylthio)ethyl]thiomethyl]-1,4-dithiane, and 2,5-bis(2,3-epithiopropylthiomethyl)-2,5-dimethyl-1,4-dithiane; aromatic 2,3-epithiopropylthio compounds such as 1,2-bis(2,3-epithiopropylthio)benzene, 1,3-bis(2,3-epithiopropylthio)benzene, 1,4-bis(2,3-epithiopropylthio)benzene, 1,2-bis(2,3-epithiopropylthiomethyl)benzene, 1,3-bis(2,3-epithiopropylthiomethyl)benzene, 1,4-bis(2,3-epithiopropylthiomethyl)benzene, bis[4-(2,3-epithiopropylthio)phenyl]methane, 2,2-bis[4-(2,3-epithiopropylthio)phenyl]propane, bis[4-(2,3-epithiopropylthio)phenyl]sulfide, bis[4-(2,3-epithiopropylthio)phenyl]sulfone, and 4,4'-bis(2,3-epithiopropylthio)biphenyl; chained aliphatic 2,3-epithiopropyloxy compounds such as bis(2,3-epithiopropyl)ether, bis(2,3-epithiopropyloxy)methane, 1,2-bis(2,3-epithiopropyloxy)ethane, 1,2-bis(2,3-epithiopropyloxy)propane, 1,3-bis(2,3-epithiopropyloxy)propane, 1,3-bis(2,3-epithiopropyloxy)-2-methylpropane, 1,4-bis(2,3-epithiopropyloxy)butane, 1,4-bis(2,3-epithiopropyloxy)-2-methylbutane, 1,3-bis(2,3-epithiopropyloxy)butane, 1,5-bis(2,3-epithiopropyloxy)pentane, 1,5-bis(2,3-epithiopropyloxy)-2-methylpentane, 1,5-bis(2,3-epithiopropyloxy)-3-thiapentane, 1,6-bis(2,3-epithiopropyloxy) hexane, 1,6-bis(2,3-epithiopropyloxy)-2-methylhexane, 1,8-bis(2,3-epithiopropyloxy)-3,6-dithiaoctane, 1,2,3-tris(2,3-epithiopropyloxy)propane, 2,2-bis(2,3-epithiopropyloxy)-1,3-bis(2,3-epithiopropyloxymethyl) propane, 2,2-bis(2,3-epithiopropyloxymethyl)-1-(2,3-epithiopropyloxy)butane, 1,5-bis(2,3-epithiopropyloxy)-2-(2,3-epithiopropyloxymethyl)-3-thiapentane, 1,5-bis(2,3-epithiopropyloxy)-2,4-bis(2,3-epithiopropyloxymethyl-3-thiapentane, 1-(2,3-epithiopropyloxy)-2,2-bis(2,3-epithiopropyloxymethyl)-4-thiahexane, 1,5,6-tris(2,3-epithiopropyloxy)-4-(2,3-epithiopropyloxymethyl)-3-thiahexane, 1,8-bis(2,3-epithiopropyloxy)-4-(2,3-epithiopropyloxymethyl)-3,6-dithiaoctane, 1,8-bis(2,3-epithiopropyloxy)-4,5-bis(2,3-epithiopropyloxymethyl)-3,6-dithiaoctane, 1,8-bis(2,3-epithiopropyloxy)-4,4-bis(2,3-epithiopropyloxymethyl)-3,6-dithiaoctane, 1,8-bis(2,3-epithiopropyloxy)-2,5-bis(2,3-epithiopropyloxymethyl)-3,6-dithiaoctane, 1,8-bis(2,3-epithiopropyloxy)-2,4,5-tris(2,3-epithiopropyloxymethyl)-3,6-dithiaoctane, 1,1,1-tris[[2-(2,3-epithiopropyloxy)ethyl]thiomethyl]-2-(2,3-epithiopropyloxy)ethane, 1,1,2,2-tetrakis[[2-(2,3-epithiopropyloxy)ethyl]thiomethyl]ethane, 1,11-bis(2,3-epithiopropyloxy)-4,8-bis(2,3-epithiopropyloxymethyl)-3,6,9-trithiaundecane, 1,11-bis(2,3-epithiopropyloxy)-4,7-bis(2,3-epithiopropyloxymethyl)-3,6,9-trithiaundecane, and 1,11-bis(2,3-epithiopropyloxy)-5,7-bis(2,3-epithiopropyloxymethyl)-3,6,9-trithiaundecane; cycloaliphatic 2,3-epithiopropyloxy compounds such as 1,3-bis(2,3-epithiopropyloxy)cyclohexane, 1,4-bis(2,3-epithiopropyloxy)cyclohexane, 1,3-bis(2,3-epithiopropyloxymethyl)cyclohexane, 1,4-bis(2,3-epithiopropyloxymethyl)cyclohexane, 2,5-bis(2,3-epithiopropyloxymethyl)-1,4-dithiane, 2,5-bis[[2-(2,3-epithiopropyloxy)ethyl]thiomethyl]-1,4-dithiane, and 2,5-bis(2,3-epithiopropyloxymethyl)-2,5-dimethyl-1,4-dithiane; and aromatic 2,3-epithiopropyloxy compounds such as 1,2-bis(2,3-epithiopropyloxy)benzene, 1,3-bis(2,3-epithiopropyloxy)benzene, 1,4-bis(2,3-epithiopropyloxy)benzene, 1,2- bis(2,3-epithiopropyloxymethyl)benzene, 1,3-bis(2,3-epithiopropyloxymethyl)benzene, 1,4-bis(2,3-epithiopropyloxymethyl)benzene, bis[4-(2,3-epithiopropyloxy)phenyl]methane, 2,2-bis[4-(2,3-epithiopropyloxy)phenyl]propane, bis[4-(2,3-epithiopropyloxy)phenyl]sulfide, bis[4-(2,3-epithiopropyloxy)phenyl]sulfone, and 4,4'-bis(2,3-epithiopropyloxy)biphenyl, and the like. It is possible to use the episulfide compound in a combination of at least one type selected from the above.

As the episulfide compound, it is preferable to use a compound represented by General Formula (1), and it is possible to use one alone or as a mixture of two or more types.

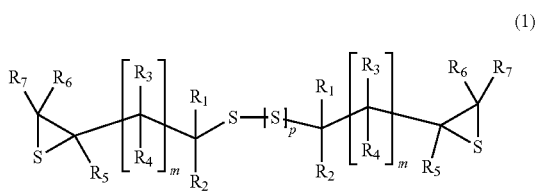

(1)

In General Formula (1), $R_1$ to $R_7$ may be the same or different and represent a hydrogen atom, a linear or branched alkyl group having 1 or more and 10 or less carbon atoms, or a substituted or unsubstituted aryl group having 6 or more and 18 or less carbon atoms. $R_1$ to $R_7$ may be the same or different. Examples of the linear or branched alkyl group having 1 or more and 10 or less carbon atoms include a methyl group, an ethyl group, an n-propyl group, an isopropyl group, an n-butyl group, a sec-butyl group, a tert-butyl group, a pentyl group, a hexyl group, a heptyl group, an octyl group, a nonyl group, a decyl group, and the like.

Examples of the aryl group include aryl groups with 6 or more and 18 or less carbon atoms such as phenyl, tolyl, xylyl, biphenyl, naphthyl, anthryl, and phenanthryl.

Examples of the substituent of the substituted aryl group include an alkyl group having 1 or more and 10 or less carbon atoms, a halogen atom, a hydroxyl group, an alkoxyl group or an alkylthio group having 1 or more and 10 or less carbon atoms, an amino group, or the like.

$R_1$ to $R_7$ may be the same or different and are preferably a hydrogen atom or a linear or branched alkyl group having 1 or more and 10 or less carbon atoms, and all are preferably hydrogen atoms.

m is an integer of 0 or more and 2 or less, preferably 0 or 1, and more preferably 0. p represents an integer of 0 or more and 4 or less, preferably 0 or 1.

In the present embodiment, it is preferable to use bis(2,3-epithiopropyl) sulfide or bis(2,3-epithiopropyl) disulfide as the episulfide compound.

In the present embodiment, in a case where the episulfide compound is subjected to a vulcanization process, it is possible for the polymerizable reactive compound to include the episulfide compound and a compound obtained by vulcanizing the episulfide compound. In the vulcanization reaction, it is possible to use sulfur in a range of 0.1 to 20% by weight with respect to the total weight of the episulfide compound. Examples of the vulcanization catalyst include imidazoles such as imidazole, 1,2-dimethylimidazole, benzylmethylimidazole, and 2-ethyl-4-imidazole, amine catalysts, and the like.

It is possible for the polymerizable reactive compound to include at least one type selected from an active hydrogen compound, an epoxy compound, a polyiso (thio) cyanate compound, or the like, in addition to the episulfide compound.

Examples of active hydrogen compounds include poly(thi)ol compounds having two or more hydroxy groups or mercapto groups, polycarboxylic acid compounds having two or more carboxyl groups, and the like. In addition, examples thereof also include a compound having two or more active hydrogen groups selected from a hydroxy group, a mercapto group, a carboxyl group, or the like in one molecule. Two or more active hydrogen groups may be the same or different.

Among the poly(thio)ol compounds, examples of the polyol compound include aliphatic polyols such as ethylene glycol, diethylene glycol, propylene glycol, dipropylene glycol, tripropylene glycol, butylene glycol, neopentyl glycol, glycerin, trimethylolethane, and trimethylolpropane; aromatic polyols such as dihydroxynaphthalene, trihydroxynaphthalene, tetrahydroxynaphthalene, dihydroxybenzene, benzenetriol, biphenyltetraol, pyrogallol, (hydroxynaphthyl)pyrogallol, trihydroxyphenanthrene, bisphenol A, bisphenol F, xylylene glycol, di(2-hydroxyethoxy)benzene, and bisphenol A-bis-(2-hydroxyethyl ether); halogenated polyols such as dibromoneopentyl glycol; and polymer polyols such as epoxy resins.

In the present embodiment, it is possible to use at least one type selected from the above in a combination.

In addition, as the polyol compound, it is also possible to use other polyol compounds such as condensation reaction products of organic acids such as oxalic acid, glutamic acid, and adipic acid, and the above polyols; addition reaction products of the polyols above and alkylene oxides such as ethylene oxide or propylene oxide; addition reaction products of an alkylene polyamine and an alkylene oxide such as ethylene oxide or propylene oxide; polyols containing a sulfur atom, and the like. It is possible to use the polyol compound in a combination of at least one type selected from the above.

Examples of polythiol compounds include aliphatic polythiol compounds such as ethylene glycol bis(3-mercaptopropionate), trimethylolpropane tris(2-mercaptoacetate), trimethylolpropane tris(3-mercaptopropionate), trimethylolethane tris(2-mercaptoacetate), pentaerythritol tetrakis(2-mercaptoacetate), pentaerythritol tetrakis(3-mercaptopropionate), bis(mercaptomethyl)sulfide, bis(mercaptomethyl) disulfide, bis(mercaptoethyl)sulfide, bis(mercaptoethyl) disulfide, bis(mercaptopropyl)sulfide, bis(mercaptomethylthio)methane, bis(2-mercaptoethylthio) methane, bis(3-mercaptopropylthio)methane, 1,2-bis(mercaptomethylthio)ethane, 1,2-bis(2-mercaptoethylthio) ethane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, tetrakis(mercaptomethylthiomethyl)methane, 1,1,3,3-tetrakis(mercaptomethylthio)propane, 1,1,2,2-tetrakis(mercaptomethylthio)ethane, and 4,6-bis(mercaptomethylthio)-1,3-dithiane; aromatic polythiol compounds having an aromatic ring; heterocyclic polythiol compounds having a heterocycle, and the like. It is possible to use the polythiol compound in a combination of at least one type selected from the above.

Examples of the polythiol compound include 4-mercaptomethyl-1,8-dimercapto-3,6-dithiaoctane, 4,8 or 4,7 or 5,7-dimercaptomethyl-1,11-dimercapto-3,6,9-trithiaundecane, pentaerythritol tetrakis mercapto acetate, pentaerythritol tetrakis mercapto propionate, 2,5-bis(mercaptomethyl)-1,4- dithiane, bis(mercaptoethyl) sulfide, 1,1,3,3-tetrakis(mercaptomethylthio)propane, 4,6-bis(mercaptomethylthio)-1,3-dithiane, and 2-(2,2-bis(mercaptomethylthio)ethyl)-1,3-dithietane are preferable, 4-mercaptomethyl-1,8-dimercapto-3,6-dithiaoctane, 4,8 or 4,7 or 5,7-dimercaptomethyl-1,11-dimercapto-3,6,9-trithiaundecane, 2,5-bis(mercaptomethyl)-1,4-dithiane, bis(mercaptoethyl)sulfide, 1,1,3,3-tetrakis(mercaptomethylthio)propane, 4,6-bis(mercaptomethylthio)-1,3-dithiane, and 2-(2,2-bis(mercaptomethylthio)ethyl)-1,3-dithietane are more preferable. It is possible to use the polythiol compound in a combination of at least one type selected from the above.

Examples of polycarboxylic acid compounds include succinic acid, adipic acid, sebacic acid, azelaic acid, dodecanedioic acid, terephthalic acid, isophthalic acid, orthophthalic acid, phthalic anhydride, tetrahydrophthalic acid, hexahydrophthalic acid, naphthalenedicarboxylic acid, biphenyl dicarboxylic acid, dimer acid, trimellitic acid, pyromellitic acid, ε-caprolactone, and the like. It is possible to use the polycarboxylic acid compound in a combination of at least one type selected from the above.

Examples of the compound having two or more different active hydrogen groups include a hydroxythiol compound having one or more mercapto groups and one or more hydroxyl groups, or the like.

Preferable examples of the epoxy compound include a compound having two or more epoxy groups, and specific examples thereof include phenolic-based epoxy compounds produced by condensation of an aromatic hydroxy compound such as phenol or bisphenol A and epihalohydrin, alcohol-based epoxy compounds produced by condensation of an alcohol compound and epihalohydrin, glycidyl ester-based epoxy compounds produced by condensation of a carboxylic acid compound and epihalohydrin, amine-based epoxy compounds produced by condensation of amine and epihalohydrin, epoxy compounds produced by oxidative epoxidation of unsaturated compounds, urethane-based epoxy compounds produced from alcohols, phenol compounds with diisocyanates, glycidol, and the like, compounds in which a part or all of the thiirane ring of the episulfide compound is substituted with an epoxy ring, and the like. It is possible to use the epoxy compound in a combination of at least one type selected from the above.

It is also possible for the polymerizable reactive compound to include a polyiso(thio)cyanate compound in addition to the episulfide compound.

The polyiso(thio)cyanate compound is not particularly limited as long as it is possible to exhibit the effects of the present invention, and it is possible to use compounds known in the related art; however, examples thereof include aliphatic polyisocyanate compounds such as tetramethylene diisocyanate, pentamethylene diisocyanate, hexamethylene diisocyanate, pentamethylene diisocyanate, octamethylene diisocyanate, 2,2,4-trimethylhexamethylene diisocyanate, 2,4,4-trimethylhexamethylene diisocyanate, lysine diisocyanatomethyl ester, lysine triisocyanate, and xylylene diisocyanate;

alicyclic polyisocyanate compounds such as isophorone diisocyanate, bis(isocyanatomethyl)cyclohexane, bis(isocyanatocyclohexyl)methane, dicyclohexyldimethylmethane isocyanate, 2,5-bis(isocyanatomethyl)bicyclo-[2.2.1]-heptane, 2,6-bis(isocyanatomethyl)bicyclo-[2.2.1]-heptane, 3,8-bis(isocyanatomethyl)tricyclodecane, 3,9-bis(isocyanatomethyl)tricyclodecane, 4,8-bis(isocyanatomethyl)tricyclodecane, and 4,9-bis(isocyanatomethyl)tricyclodecane;

aromatic polyisocyanate compounds such as tolylene diisocyanate, 4,4'-diphenylmethane diisocyanate, diphenyl sulfide-4,4-diisocyanate, and phenylene diisocyanate;

heterocyclic polyisocyanate compounds such as 2,5-diisocyanatothiophene, 2,5-bis(isocyanatomethyl)thiophene, 2,5-diisocyanatotetrahydrothiophene, 2,5-bis(isocyanatomethyl)tetrahydrothiophene, 3,4-bis(isocyanatomethyl)tetrahydrothiophene, 2,5-diisocyanato-1,4-dithiane, 2,5-bis(isocyanatomethyl)-1,4-dithiane, 4,5-diisocyanato-1,3-dithiolane, and 4,5-bis(isocyanatomethyl)-1,3-dithiolane;

aliphatic polyisothiocyanate compounds such as hexamethylene diisothiocyanate, lysine diisothiocyanate methyl ester, lysine triisothiocyanate, xylylene diisothiocyanate, bis(isothiocyanatomethyl)sulfide, bis(isothiocyanatoethyl)sulfide, and bis(isothiocyanatoethyl)disulfide;

alicyclic polyisothiocyanate compounds such as isophorone diisothiocyanate, bis(isothiocyanatomethyl)cyclohexane, bis(isothiocyanatocyclohexyl)methane, cyclohexane diisothiocyanate, methylcyclohexane diisothiocyanate, 2,5-bis(isothiocyanatomethyl)bicyclo-[2.2.1]-heptane, 2,6-bis(isothiocyanatomethyl)bicyclo-[2.2.1]-heptane, 3,8-bis(isothiocyanatomethyl)tricyclodecane, 3,9-bis(isothiocyanatomethyl)tricyclodecane, 4,8-bis(isothiocyanatomethyl)tricyclodecane, and 4,9-bis(isothiocyanatomethyl)tricyclodecane;

aromatic polyisothiocyanate compounds such as tolylene diisothiocyanate, 4,4-diphenylmethane diisothiocyanate, and diphenyl disulfide-4,4-diisothiocyanate;

sulfur-containing heterocyclic polyisothiocyanate compounds such as 2,5-diisothiocyanatothiophene, 2,5-bis(isothiocyanatomethyl)thiophene, 2,5-isothiocyanatotetrahydrothiophene, 2,5-bis(isothiocyanatomethyl)tetrahydrothiophene, 3,4-bis(isothiocyanatomethyl)tetrahydrothiophene, 2,5-diisothiocyanato-1,4-dithiane, 2,5-bis(isothiocyanatomethyl)-1,4-dithiane, 4,5-diisothiocyanato-1,3-dithiolane, and 4,5-bis(isothiocyanatomethyl)-1,3-dithiolane, and the like. It is possible for the polyiso(thio)cyanate compound to include at least one type selected from the above.

In addition, it is also possible to use these chlorine-substituted compounds, halogen-substituted compounds such as bromine-substituted compounds, alkyl-substituted compounds, alkoxy-substituted compounds, nitro-substituted compounds and prepolymer modified products with polyhydric alcohols, carbodiimide modified products, urea modified products, buret modified products, dimerization or trimerization reaction products, and the like.

The polyiso(thio)cyanate compound is preferably a polyisocyanate compound, and it is preferable to include at least one type selected from 2,5-bis(isocyanatomethyl)bicyclo-[2.2.1]-heptane, 2,6-bis(isocyanatomethyl)bicyclo-[2.2.1]-heptane, xylylene diisocyanate, bis(isocyanatocyclohexyl)methane, bis(isocyanatomethyl)cyclohexane, 4,4'-diphenylmethane diisocyanate, isophorone diisocyanate, hexamethylene diisocyanate, and pentamethylene diisocyanate.

In a case where the polymerizable reactive compound is a combination of an episulfide compound and another polymerizable reactive compound, a combination of an episulfide compound and a polyiso(thio)cyanate compound, a combination of an episulfide compound and an active hydrogen compound, and a combination of an episulfide compound, a polyiso(thio)cyanate compound, and an active hydrogen compound are preferable. As the active hydrogen compound, a polythiol compound is preferable.

It is possible to set the molar ratio of the functional group of the episulfide compound to 60 or more with respect to 100 by mole of a total of the functional group moles of the polymerizable reactive compound, preferably 75 or more, and more preferably 85 or more.

As described above, even in a case where a polymerizable composition including a large amount of a highly reactive episulfide compound is used, according to the method for setting polymerization condition of the present embodiment, it is possible to set conditions under which excessive polymerization and side reactions are suppressed and to manufacture a lens with reduced striae.

A more detailed description will be given of the cured resin forming the optical material in the present embodiment. The cured resin is obtained by heating and polymerizing a composition which includes a polymerizable reactive compound including an episulfide compound, and a polymerization catalyst, and is preferably a cured resin obtained from a liquid composition for which a casting operation is easy.

[Other Components Such as Additives]

The polymerizable composition used in the present embodiment may include components other than the polymerizable reactive compound described above and modifiers such as a polyether-modified compound, an ester compound, or an ether compound.

Examples thereof include a monofunctional iso(thio)cyanate compound, a monofunctional (thio)epoxy compound, a monofunctional oxetanyl compound, a monofunctional thietanyl compound, a monofunctional (meth)acryloyl compound having one functional group freely selected from a methacryloyloxy group, an acryloyloxy group, a methacryloylthio group, an acryloylthio group, a methacrylamide group, or an acrylamide group, a monofunctional alkene compound having one polymerizable carbon-carbon double bond other than a methacryloyloxy group, an acryloyloxy group, a methacryloylthio group, an acryloylthio group, a methacrylamide group, or an acrylamide group, a monofunctional alcohol compound other than alcohol used as a solvent, a monofunctional thiol compound, a monofunctional carboxylic acid compound having one carboxyl group, a solvent, moisture, and the like.

In addition, from the viewpoint of adjusting the optical characteristics, it is also possible to mix the episulfide compound used in the present embodiment and an inorganic compound including a sulfur atom, and carry out polymerization and curing, to mix the episulfide compound, the inorganic compound including a sulfur atom, and the active hydrogen compound described above (preferably the thiol compound described above) and carry out polymerization and curing, and, further, to mix an episulfide compound, a compound obtained by vulcanizing the episulfide compound, and the active hydrogen compound described above (preferably the thiol compound described above) and carry out polymerization and curing.

Specific examples of the inorganic compound including a sulfur atom include sulfur, hydrogen sulfide, carbon disulfide, selenocarbon sulfide, ammonium sulfide, sulfur oxides such as sulfur dioxide and sulfur trioxide, thiocarbonates, sulfuric acid and salts thereof, halides such as hydrogen sulfide, sulfite, hyposulfite, persulfate, thiocyanate, thiosulfate, sulfur dichloride, thionyl chloride, and thiophosgene, boron sulfide, nitrogen sulfide, silicon sulfide, phosphorus sulfide, arsenic sulfide, selenium sulfide, metal sulfide, metal hydrosulfide, and the like. These may be used alone or two or more types may be mixed and used. Sulfur is preferable. The added amount is used in the range of 0.1 to 20% by weight with respect to the total weight of the composition containing the episulfide compound.

In the process of carrying out casting polymerization of the composition to manufacture a molded article in the present embodiment, a polymerization catalyst is added for curing by heat.

Examples of the polymerization catalyst include amines, phosphines, organic acids and salts thereof, esters, anhydrides, inorganic acids, quaternary ammonium salts, quaternary phosphonium salts, tertiary sulfonium salts, secondary iodonium salts, Lewis acids, radical polymerization catalysts, cationic polymerization catalysts, and the like.

The polymerization catalyst described above may be used alone or in a mixture of two or more types, and among these polymerization catalysts, when two or more types having different reactivity are used together, the handling property of the polymerizable composition, the optical property of the obtained resin, hue, and transparency may be improved and the optical distortion and striae may be suppressed, which is preferable.

Specific examples of preferable polymerization catalysts include tertiary amines such as triethylamine, tri-n-propylamine, triisopropylamine, tri-n-butylamine, tri-isobutylamine, N,N-dimethylbenzylamine, N-methylmorpholine, N,N-dimethylcyclohexylamine, N,N-dicyclohexylmethylamine, dimethyldipropylenetriamine, pentamethyldiethylenetriamine, bis(2-dimethylaminoethyl) ether, N-methylmorpholine, N,N'-dimethylpiperazine, triethylenediamine, N,N,N',N'-tetramethylethylenediamine, and bicyclooctanediamine (DABCO); quaternary ammonium salts such as tetramethyl ammonium bromide, tetraethyl ammonium bromide, tetrapropyl ammonium bromide, tetrabutyl ammonium bromide, tetrahexyl ammonium bromide, and tetraethyl ammonium hydroxide; imidazoles such as imidazole, 1,2-dimethylimidazole, benzylmethylimidazole, 2-ethyl-4-imidazole; pyrazoles such as pyrazole and 3,5-dimethylpyrazole; hindered amines such as 1,2,2,6,6-pentamethyl-4-piperidinol, 1,2,2,6,6-pentamethyl-4-hydroxyethyl-4-piperidinol, methyl-1,2,2,6,6-pentamethyl-4-piperidyl sebacate, mixtures of methyl-1,2,2,6,6-pentamethyl-4-piperidyl sebacate and bis(1,2,2,6,6-pentamethyl-4-piperidyl) sebacate, bis(1,2,2,6,6-pentamethyl-4-piperidyl) sebacate, bis(2,6,6-tetramethyl-1-(octyloxy)-4-piperidyl) sebacate, bis(1,2,2,6,6-pentamethyl-4-piperidyl)[[3,5-bis(1,1-dimethylethyl)-4-hydroxyphenyl]methyl]butylmalonate, and tetrakis(1,2,2,6,6-pentamethyl-4-piperidyl)butane-1,2,3,4-tetracarboxylate; and quaternary phosphonium salts such as tetra-n-butylphosphonium bromide, tetrabutylphosphonium chloride, and trioctylethylphosphonium bromide.

In addition, examples thereof include phosphines such as trimethylphosphine, triethylphosphine, tri-n-propylphosphine, triisopropylphosphine, tri-n-butylphosphine, triphenylphosphine, tribenzylphosphine, 1,2-bis(diphenylphosphino)ethane, and 1,2-bis(dimethylphosphino)ethane; Lewis acids such as dimethyltin dichloride, dibutyltin dichloride, dibutyltin dilaurate, tetrachlorotin, dibutyltin oxide, zinc chloride, acetylacetone zinc, aluminum chloride, aluminum fluoride, triphenylaluminum, tetrachlorotitanium, and calcium acetate; cationic polymerization catalysts such as diphenyliodonium hexafluorophosphoric acid, diphenyliodonium hexafluoroarsenic acid, diphenyliodonium hexafluoroantimony, triphenylsulfonium tetrafluoroboric acid, triphenylsulfonium hexafluorophosphoric acid, triphenylsulfonium hexafluoroarsenic acid, and the like, without being limited to these exemplified compounds.

These polymerization catalysts may be used alone or in a mixture of two or more types.

The added amount of the polymerization catalyst is used in the range of 0.001 to 10% by weight with respect to the total weight of the composition containing the episulfide compound, and preferably in the range of 0.01 to 1% by weight.

In addition, in the process of cast polymerizing the composition of the present embodiment to manufacture a molded article, an internal release agent may be added as necessary.

As the internal release agent, it is possible to use an acidic phosphate ester. Examples of acidic phosphate esters include phosphoric monoesters and phosphoric acid diesters, which may be used alone or in a combination of two or more types.

It is possible to represent the acidic phosphate ester used as an internal release agent by General Formula (a).

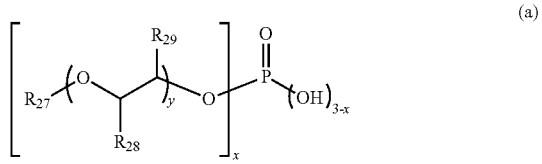

In General Formula (a), x represents an integer of 1 or 2, y represents an integer of 0 to 18, $R_{27}$ represents an alkyl group having 1 to 20 carbon atoms, and $R_{28}$ and $R_{29}$ each independently represents a hydrogen atom, a methyl group, or an ethyl group. The number of carbon atoms in [ ]x is preferably 4 to 20. A plurality of present $R_{27}$, a plurality of present $R_{28}$, or a plurality of present $R_{29}$ may be the same or different from each other.

Examples of $R_{27}$ in General Formula (a) include organic residues derived from linear aliphatic compounds such as methane, ethane, propane, butane, pentane, hexane, heptane, octane, nonane, decane, undecane, dodecane, tetradecane, and hexadecane; organic residues derived from branched chain aliphatic compounds such as 2-methylpropane, 2-methylbutane, 2-methylpentane, 3-methylpentane, 3-ethylpentane, 2-methylhexane, 3-methylhexane, 3-ethylhexane, 2-methylheptane, 3-methylheptane, 4-methylheptane, 3-ethylheptane, 4-ethylheptane, 4-propylheptane, 2-methyloctane, 3-methyloctane, 4-methyloctane, 3-ethyloctane, 4-ethyloctane, and 4-propyloctane; organic residues derived from alicyclic compounds such as cyclopentane, cyclohexane, 1,2-dimethylcyclohexane, 1,3-dimethylcyclohexane, and 1,4-dimethylcyclohexane, and the like and it is possible to use at least one type selected from the above. The present invention is not limited only to these exemplified compounds. It is possible to use at least one type or a mixture of two or more types of acidic phosphate esters.

In General Formula (a) described above, y is preferably 0 or 1.

In a case where y is 0, $R_{27}$ is preferably a linear or branched alkyl group having 4 to 12 carbon atoms, and more preferably a linear alkyl group having 4 to 12 carbon atoms.

In a case where y is 1, $R_{27}$ is preferably a linear or branched alkyl group having 1 to 20 carbon atoms, and is preferably a linear or branched alkyl group having 3 to 12 carbon atoms.

It is possible to use the acidic phosphate ester as one type or a mixture of two or more types selected from the above.

Examples of acidic phosphate esters include ZelecUN (manufactured by STEPAN), internal release agents for MR (manufactured by Mitsui Chemicals, Inc)., the JP series manufactured by Johoku Chemical Co., Ltd., the phosphanol series manufactured by Toho Chemical Industry Co., Ltd., the AP and DP series manufactured by Daihachi Chemical Industry Co., Ltd., and ZelecUN (manufactured by STEPAN), and internal release agents for MR (manufactured by Mitsui Chemicals, Inc.) are more preferable.

In order that the molded article formed of the cured resin in the present embodiment does not deteriorate even when exposed to the outside for a long period of time, it is desirable to further add an ultraviolet absorber and a hindered amine light stabilizer to the composition in the present embodiment to impart weatherability thereto.

The ultraviolet absorber described above is not particularly limited, and, for example, it is possible to use various ultraviolet absorbers such as a benzotriazole-based ultraviolet absorber, a triazine-based ultraviolet absorber, a benzophenone-based ultraviolet absorber, a benzoate-based ultraviolet absorber, a propanedioic acid ester-based ultraviolet absorber, or an oxanilide-based ultraviolet absorber.

Specifically, examples of ultraviolet absorbers include benzotriazole-based ultraviolet absorbers such as 2-(2H-benzotriazol-2-yl)-4-methyl-6-(3,4,5,6-tetrahydrophthalibidylmethyl)phenol, 2-(2H-benzotriazole-2-yl)-p-cresol, 2-(2H-benzotriazole-2-yl)-4-tert-butylphenol, 2-(2H-benzotriazole-2-yl)-4,6-di-tert-butylphenol, 2-(2H-benzotriazole-2-yl)-4,6-bis(1-methyl-1-phenyl ethyl)phenol, 2-(2H-benzotriazole-2-yl)-4-(1,1,3,3-tetramethylbutyl)-6-(1-meth yl-1-phenyl ethyl)phenol, 2-(2H-benzotriazole-2-yl)-4-(3-on-4-oxa-dodecyl)-6-tert-butyl-phenol, 2-{5-chloro (2H)-benzotriazole-2-yl}-4-(3-on-4-oxa-dodecyl)-6-tert-butyl-phenol, 2-{5-chloro(2H)-benzotriazole-2-yl}-4-methyl-6-tert-butyl-phenol, 2-(2H-benzotriazole-2-yl)-4,6-di-tert-pentylphenol, 2-{5-chloro (2H)-benzotriazole-2-yl}-4,6-di-tert-butylphenol, 2-(2H-benzotriazole-2-yl)-4-tert-octylphenol, 2-(2H-benzotriazole-2-yl)-4-methyl-6-n-dodecyl phenol, 3-[3-tert-butyl-5-(5-chloro-2H-benzotriazole-2-yl)-4-hydroxyphenyl]octyl propionic acid, 3-[3-tert-butyl-5-(5-chloro-2H-benzotriazole-2-yl)-4-hydroxyphenyl]propionic acid 2-ethylhexyl, reaction products of methyl-3-{3-(2H-benzotriazole-2-yl)-5-tert-butyl-4-hydroxyphenyl}propionate/polyethylene glycol 300, trade name Viosorb 583 (manufactured by Kyodo Chemical Co., Ltd), trade name Tinuvin 326 (manufactured by BASF), trade name Tinuvin 384-2 (manufactured by BASF), trade name Tinuvin PS (manufactured by BASF), trade name Seesorb 706 (manufactured by Shipro Kasei Kaisha, Ltd), and trade name Eversorb 109 (manufactured by Everlight); triazine-based ultraviolet absorbers such as 2-(4-phenoxy-2-hydroxy-phenyl)-4,6-diphenyl-1,3,5-triazine, 2-(2-hydroxy-4-oxa-hexadecyloxy)-4,6-di(2,4-dimethyl-phenyl)-1,3,5-triazine, 2-(2-hydroxy-4-oxa-heputadecyloxy)-4,6-di(2,4-dimethyl-phenyl)-1,3,5-triazine, 2-(2-hydroxy-4-isooctyloxy-phenyl)-4,6-di(2,4-dimethyl-phenyl)-1,3,5-triazine, trade name Tinuvin 400 (manufactured by BASF), trade name Tinuvin 405 (manufactured by BASF), trade name Tinuvin 460 (manufactured by BASF), and trade name Tinuvin 479 (manufactured by BASF); benzophenone-based ultraviolet absorbers such as 2-hydroxy-4-n-methoxybenzophenone and 2-hydroxy-4-n-octoxybenzophenone; benzoate-based ultraviolet absorbers such as 2,4-di-tert-butyl phenyl-3,5-di-tert-butyl-4-hydroxybenzoate; propanedioccitan acid ester-based ultraviolet absorbers such as propanedioccitan acid-{(4-methoxyphenyl)-methylene}-dimethyl ester, trade name Hostavin PR-25 (manufactured by Clariant Japan Co., Ltd), and trade name Hostavin B-CAP (manufactured by Clariant Japan Co., Ltd); oxanilide-based ultraviolet absorbers such as 2-ethyl-2'-ethoxy-oxanilide, trade name Sanduvor VSU (manufactured by Clariant Japan Co., Ltd); and the like. Among these ultraviolet absorbers, benzotriazole-based and triazine-based ultraviolet absorbers tend to be preferable.

Furthermore, a light-control dye or a light-control pigment may be added for the purpose of imparting light-control properties. It is possible to use one type or two or more types from representative light-control dyes or light-control pigments from spiropyran-based compounds, spirooxazine-based compounds, fulgide-based compounds, naphthopyran-based compounds, and bisimidazole compounds, according to the desired coloration.

To the composition of the present embodiment, various additives may be further added as necessary, such as a polymerization accelerator, a catalyst, an infrared absorber, a radical scavenger, an antioxidant, a polymerization inhibitor, a non-light-control pigment and dye, a binder, a dispersant, an antifoaming agent, and nanometer-sized organic or inorganic particles.

A cured resin obtained by heating and polymerizing the composition of the present embodiment and a molded article formed of the resin are manufactured by adding a polymerizable reactive compound including an episulfide compound and, as necessary, the various additives and the like described above. In addition, a polymerizable reactive compound other than the polymerizable reactive compound, an additive, and the like, which are not described in the present application may be added to the composition in the present embodiment as long as the effects of the present invention are not impaired.

A description will be given below of the method for setting polymerization condition and the polymerization condition setting device 10 according to the present embodiment.

Figure 2:
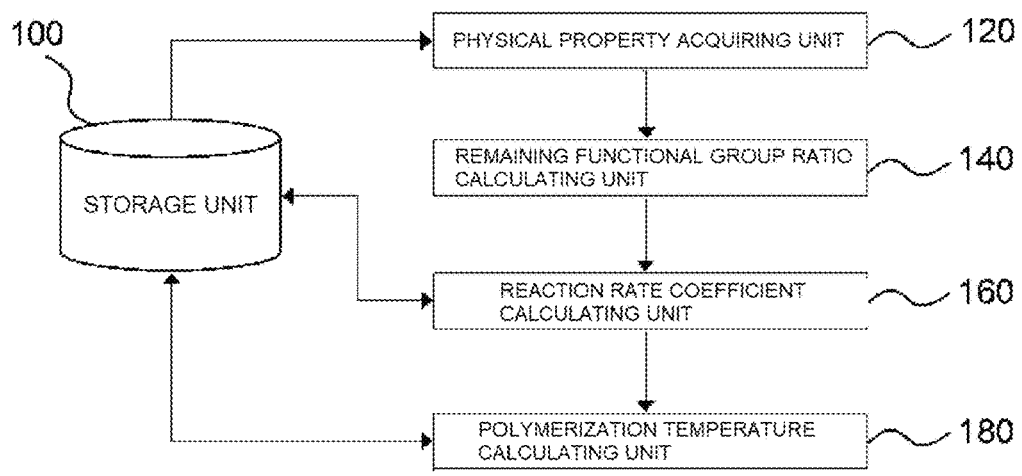
FIG. 2 is a block diagram illustrating a configuration of a polymerization condition setting device according to the present embodiment.

FIG. 2 is a block diagram illustrating a configuration of the polymerization condition setting device 10 according to the present embodiment. The setting apparatus 10 according to the present embodiment is a setting apparatus which calculates polymerization conditions for the composition described above.

The setting apparatus 10 is provided with the physical property acquiring unit 120, the remaining functional group ratio calculating unit 140, the reaction rate coefficient calculating unit 160, and the polymerization temperature calculating unit 180.

The polymerization condition setting device 10 is further provided with the storage unit 100. The storage unit is a computer-readable medium which is able to record the measurement results, the calculation results, and a program. Examples thereof include a semiconductor memory, an IC card, an optical disc, a magnetic disk, a magneto-optical disc, a magnetic tape, a digital video disk, and the like. The program recorded in the storage unit enables the computer to realize the method for setting polymerization condition of the present embodiment.

The physical property acquiring unit 120 acquires a physical property value a derived from a functional group of the polymerizable reactive compound before heating and a physical property value b derived from a remaining functional group after maintaining heat for a predetermined time in a case of heating a composition which includes a polymerizable reactive compound including an episulfide compound, and a polymerization catalyst and maintaining a predetermined temperature. The remaining functional group ratio calculating unit 140 calculates a remaining functional group ratio from the physical property value a and the physical property value b. The reaction rate coefficient calculating unit 160 calculates a reaction rate coefficient from the remaining functional group ratio, based on a reaction rate equation. The polymerization temperature calculating unit 180 calculates a polymerization temperature based on the reaction rate coefficient and conditions below.

Conditions: When a polymerization ratio is in a range of 0% or more and 20% or less, a polymerization rate is more than 0%/hr and 3.0%/hr or less, and a standard deviation is 0.8%/hr or less.

A detailed description will be given below.

The physical property acquiring unit 120 acquires the physical property value a derived from a functional group of the polymerizable reactive compound before heating including an episulfide compound and the physical property value b derived from a remaining functional group after maintaining heat at a predetermined temperature for a predetermined time, for example, from the storage unit 100, in a case of heating the composition and maintaining a predetermined temperature (physical property acquiring step S10).

The temperature at which the polymerizable reactive compound including an episulfide compound is heated varies depending on the temperature at which the polymerizable reactive compound is polymerized and, for example, it is possible to select one or more temperatures from a range of −10° C. or higher and 140° C. or lower. The heat maintenance time varies according to the temperature being maintained and is not particularly limited as long as the polymerization is not completed.

In addition, in a case of vulcanizing an episulfide compound using a vulcanization catalyst, it is possible to prepare a composition by mixing an episulfide compound, a compound in which the episulfide compound is vulcanized, a polymerization catalyst, and the active hydrogen compound described above (preferably the thiol compound described above) as necessary, and to heat the composition to obtain a physical property value a before heating and a physical property value b after heating of the polymerizable reactive compound.

In a composition formed of a combination of the polymerizable reactive compound, which includes an episulfide compound, and a polymerization catalyst described above, the storage unit 100 stores the physical property value a derived from a functional group of the polymerizable reactive compound before heating and the physical property value b derived from a remaining functional group after maintaining heat for a predetermined time at a predetermined temperature. The physical property value b is stored in association with the heat maintenance temperature (the temperature after heating) and is present with respect to at least one period of elapsed time for every one of a plurality of heat maintenance temperatures. The physical property value a and physical property value b are directly input to the storage unit 100 from an input unit (not shown).

The stored physical property values are the heat value, a specific gravity, a weight average molecular weight, a number average molecular weight, a $^1$H-NMR spectral intensity, or a $^{13}$C-NMR spectral intensity.

It is possible for the physical property acquiring unit 120 to read and acquire the physical property value a and the physical property value b stored in the storage unit 100, for example. It is also possible for the physical property value a and physical property value b obtained by measuring devices such as a thermal analyzer, a specific gravity measuring device, a GPC measuring device, and an NMR device to be directly input to the physical property acquiring unit 120 from an input unit (not shown).

Specific examples of a thermal analyzer able to be used in the present embodiment include a differential scanning calorimeter, a calorimeter, a microcalorimeter, a differential thermal analyzer, a differential simultaneous thermo-gravimeteric analyzer, a thermogravimetric analyzer, a thermomechanical measuring device, a dynamic thermomechanical measuring device, and the like.

Next, the remaining functional group ratio calculating unit 140 acquires the physical property value a and the physical property value b from the physical property acquiring unit 120 and calculates the remaining functional group ratio based on these physical property values (remaining functional group ratio calculating step S20).

A description will be given below of a case where the remaining functional group ratio calculating unit 140 calculates the remaining functional group ratio according to, for example, the amount of heat measured by thermal analysis.

It is possible to represent the remaining functional group ratio by Equation 1.

Remaining functional group ratio=$Xt/X_0$    Equation 1:

$X_0$ (J/g): Amount of heat measured by DSC thermal analysis of the prepared solution immediately after preparation (before polymerization)

Xt (J/g): Amount of heat of the prepared solution after heat maintenance at a specific temperature for t hours In the present embodiment, $X_0$ corresponds to the physical property value a and Xt corresponds to the physical property value b.

For example, in a case of calculating the remaining functional group ratio based on the specific gravity, it is possible to represent the remaining functional group ratio by Equation 2.

Remaining functional group ratio=[1−[(specific gravity measured after maintenance at a specific temperature for *t* hours−specific gravity of prepared solution immediately after preparation (before heating))/Δ*d*]]    Equation 2:

Δ*d*(increased amount in specific gravity for each 1% decrease in remaining functional groups)=[(specific gravity of cured resin-specific gravity of liquid immediately after preparation)/100

In the present embodiment, the specific gravity of the prepared solution immediately after the preparation (before heating) corresponds to the physical property value a, while the specific gravity measured after maintenance at a specific temperature for t hours corresponds to the physical property value b.

The reaction rate coefficient calculating unit 160 acquires the remaining functional group ratio from the remaining functional group ratio calculating unit 140, performs a kinetic analysis on the remaining functional group ratio based on the reaction rate equation, and calculates the reaction rate coefficient (reaction rate coefficient calculating step S30).

It is possible for the reaction rate coefficient calculating unit 160 to read a reaction rate equation stored in the storage unit 100 in advance.

Examples of reaction rate equations include an nth-order reaction rate equation (n is 0 or more), a Prout-Tompkins rate equation, a Bawn rate equation, a Leeson-Mattocks rate equation, and the like. It is possible for the reaction rate coefficient calculating unit 160 to select an optimal equation based on the polymerizable composition and the order of the reaction.

The reaction rate coefficient calculating unit 160 calculates a reaction rate coefficient based on the reaction rate equation read from the storage unit 100 and based on the remaining functional group ratio acquired from the remaining functional group ratio calculating unit 140. A description will be given below of a case where the n-th order reaction rate equation represented by Equation 3 is used.

kt=f(remaining functional group ratio)    Equation 3:

k: nth order reaction rate coefficient (n is a real number which is 0 or more)

t: Heat maintenance time f (remaining functional group ratio) is determined by the value of n with a function of the remaining functional group ratio.

In a graph in which the horizontal axis represents the heat maintenance time t and the vertical axis represents f (remaining functional group ratio) into which the remaining functional group ratio of the target substance (polymerizable reactive compound including the episulfide compound) in the sample is substituted, the reaction rate coefficient calculating unit 160 plots the remaining functional group ratio for each heat maintenance time. The reaction rate coefficient calculating unit 160 acquires a regression line from the graph and acquires the slope of the regression line as the reaction rate coefficient k.

To determine the correlation relationship between the reaction rate coefficient of the change in the polymerizable reactive compound, which includes the episulfide compound, included in the sample and the temperature of the sample, for example, with the temperature of the sample during heat maintenance being converted to the absolute temperature T and the reciprocal thereof on the horizontal axis and the natural logarithm of the reaction rate coefficient k at this temperature on the vertical axis, each point is plotted to obtain a regression line having a slope of (−Ea/R). This plot is called an Arrhenius plot.

Specifically, in a graph in which the vertical axis is Ln (k) and the horizontal axis is the reciprocal of the absolute temperature, the reaction rate coefficient calculating unit 160 determines Ln (k) based on the obtained reaction rate coefficient and creates an Arrhenius plot by plotting in the table. From the Arrhenius plot, a regression line and a regression line equation of Equation 4 are obtained.

y=ax+b(regression line)    Equation 4:

To predict the remaining functional group ratio, for example, the reciprocal of the desired absolute temperature T is substituted into the regression line determined as described above to calculate the reaction rate coefficient k at the absolute temperature T and, by substituting this reaction rate coefficient into the reaction rate equation illustrated in Equation 3 determined as described above, the remaining functional group ratio in a case where the sample is placed at the absolute temperature T for t hours is calculated.

Specifically, the reaction rate coefficient calculating unit 160 obtains Equation 5 by replacing y, a, x, and b in the regression line of Equation 4 with the following.

y=Ln(*k*)

a=(−Ea/R)

x=(1/T)

b=Ln(frequency factor)

Ea: Activation energy (J mol$^{-1}$K$^{-1}$)
R: Gas coefficient (8.3145 J mol$^{-1}$)
T: Absolute temperature
A: Frequency factor $$\mathrm{Ln}(k)=(-Ea/R)\times(1/T)+\mathrm{Ln}(A) \qquad \text{Equation 5:}$$

The reaction rate coefficient calculating unit 160 further obtains Equation 6 and calculates the reaction rate coefficient at the temperature used as the polymerization temperature using Equation 5 and Equation 6.

$$k=\mathrm{EXP}(y) \qquad \text{Equation 6:}$$

It is also possible for the reaction rate coefficient calculating unit 160 to calculate the polymerization ratio from Equation 7.

$$\text{Polymerization ratio (\%)}=(1-\text{remaining functional group ratio})\times 100 \qquad \text{Equation 7:}$$

The polymerization temperature calculating unit 180 acquires the reaction rate coefficient from the reaction rate coefficient calculating unit 160 and calculates the polymerization temperature based on the following polymerization conditions (polymerization temperature calculating step S40).

(Polymerization Conditions)

In a range where the polymerization ratio is 0% or more and 20% or less, the polymerization rate is more than 0%/hr and 3.0%/hr or less, and the standard deviation of the polymerization rate every predetermined time is 0.8%/hr or less.

It is possible to use the compound represented by General Formula (1) as the episulfide compound. In General Formula (1), preferable polymerization conditions are different in a case of a sulfide body in which p is 0 or in a case of a polysulfide body in which p is an integer of 1 or more and 4 or less, and, with a polysulfide body, it is possible to obtain a lens having no striae even under polymerization conditions where the polymerization rate is faster. The polysulfide body is preferably a disulfide body in which p is 1.

In the case of a sulfide body, in the range of a polymerization ratio of 0% or more and 20% or less, preferably, the polymerization rate is more than 0.5%/hr and 2.0%/hr or less, and the standard deviation of the polymerization rate every predetermined time is 0.8%/hr or less.

In a case of a polysulfide body, in the range of a polymerization ratio of 0% or more and 20% or less, preferably, the polymerization rate is more than 0.5%/hr and 3.0%/hr or less, and the standard deviation of the polymerization rate every predetermined time is 0.8%/hr or less.

In addition, the preferable polymerization conditions are also different in a case of using a compound in which a (poly) sulfide body is subjected to a vulcanization process. In the present embodiment, the compound in which the (poly)sulfide body is subjected to a vulcanization process includes a (poly)sulfide body and a compound in which the (poly)sulfide body is vulcanized.

In a case where the sulfide body is a compound subjected to a vulcanization process, when the polymerization ratio is in the range of 0% or more and 20% or less, preferably, the polymerization rate is more than 0.5%/hr and 2.0%/hr or less, and the standard deviation of the polymerization rate (slope) every predetermined time is 0.8%/hr or less.

In a case where the polysulfide body is a compound subjected to a vulcanization process, when the polymerization ratio is in the range of 0% or more and 20% or less, preferably, the polymerization rate is more than 0.5%/hr and 3.0%/hr or less, and the standard deviation of the polymerization rate (slope) every predetermined time is 0.8%/hr or less.

In the present embodiment, it is possible to obtain specific polymerization conditions by the following steps. It is possible to appropriately adopt the preferable conditions described above.

The average polymerization rate from the point where the polymerization ratio is 0% to the point where the polymerization ratio is 20% is determined by being selected from a range of more than 0%/hr and 3.0%/hr or less, calculating multiple polymerization rates every predetermined time in the time when the polymerization ratio is 0% or more and 20% or less, calculating the standard deviation, which is the positive square root of the variance of the plurality of polymerization rates and the average polymerization rate, and setting the calculated standard deviation to 0.8%/hr or less.

It is possible to calculate the average polymerization rate from the point where the polymerization ratio is 0% to the point where the polymerization ratio is 20% by (20%−0%)/(t2−t1) when the time when the polymerization ratio is 0% is t1 (hr) and the time when the polymerization ratio is 20% is t2 (hr).

When calculating how the polymerization ratio increases over time in the polymerization reaction (in other words, how the concentration of the polymerizable remaining functional group decreases), calculations are carried out sequentially at each time.

In the simulation of the present embodiment, the reaction temperature is calculated by calculating the reaction rate coefficient at the next time (t+Δt) based on the temperature and the concentration of the polymerizable remaining functional group at the time t. In the present embodiment, the temperature is the target to be calculated and it is possible to determine a temperature transition which gives a desired polymerization transition by calculation.

In the present embodiment, in the time section from the time t to immediately before the next time (t+Δt) (the region where the time value is t or more and less than t+Δt), the reaction rate (polymerization rate) is set to v which is initially set, then, the reaction rate coefficient at the next time (t+Δt) is determined so as to satisfy the condition that the reaction rate at the next time (t+Δt) is also equal to v.

For example, in the reaction of an episulfide compound, if the concentration of the episulfide functional group is A, the reaction rate (polymerization rate) v is expressed as $$v=k(T(t))\times A(t) \qquad \text{Equation a}$$

Here, k is a function of temperature.

Both the temperature T and the concentration A are functions of the time t and are represented as T(t) and A(t). v is a reaction rate (average polymerization rate) and is a value selected from the range of more than 0%/hr and 3.0%/hr or less in the present embodiment.

Then, Equation a is transformed as follows to perform the calculation.

$$k(T(t))=v/A(t) \qquad \text{Equation a'}$$

In the present embodiment, the temperature transition is determined by calculation so as to obtain the desired polymerization transition. Specifically, as described above, the reaction rate coefficient to be adopted at the time t+Δt is calculated based on the temperature and the concentration of the remaining functional group at the time t.

In Equation a', as the time advances by Δt, the concentration A of the polymerizable remaining functional group decreases, thus, in order to keep v=constant, it is necessary to increase the value of k(T(t)) and the determination is carried out by calculating how to change the value of k(T(t)).

A specific description will be given below of the calculation for determining k at the time (t+Δt) based on the parameter at the time t.

At time (t+Δt), Equation a' is as follows.

$$k(T(t+\Delta t))=v/A(t+\Delta t) \quad \text{Equation b}$$

The polymerization rate in the time section equal to more than the time t and less than (t+Δt) is the selected average polymerization rate value and is expressed as follows.

$$A(t+\Delta t)=A(t)-v\times\Delta t \quad \text{Equation c}$$

When Equation b is transformed based on Equation c, Equation d below is obtained.

$$k(T(t+\Delta t))=v/(A(t)-v\times\Delta t) \quad \text{Equation d}$$

k (T(t)) and A(t) are known values already determined by calculation in sequential calculation.

Next, the temperature (T(t+Δt)) is back-calculated from this k(T(t+Δt)).

Back-calculation is performed using the following Arrhenius equation described as Equation 5.

$$\mathrm{Ln}(k)=(-Ea/R)\times(1/T)+\mathrm{Ln}(A) \quad \text{Equation 5:}$$

Ea: Activation energy (J·mol$^{-1}$K$^{-1}$)
R: Gas coefficient (8.3145 J·mol-1)
T: absolute temperature
A: frequency factor It is possible to uniquely calculate the value of T from the calculated value of k(T(t+Δt)).

In the present embodiment, as described above, it is possible to calculate T (t+Δt) to be adopted at the time t+Δt based on various types of parameters (k(T(t)), A(t)) at the time t.

Then, each polymerization temperature (a plurality of T(t+Δt)) back-calculated every predetermined time satisfies conditions in which a standard deviation which is a positive square root of the variance of the plurality of polymerization rates calculated every predetermined time and the average polymerization rate is 0.8%/hr or less.

In the range where the polymerization ratio is more than 20% to 90%, the polymerization conditions are not particularly limited, but in view of productivity, after the polymerization temperature calculating step, it is possible to include a polymerization time setting step of selecting the reaction time when the polymerization ratio is more than 20% to 90% from 0.1 to 150 hours. In the present embodiment, in this step, in a range where a polymerization ratio is more than 20% and 90% or less and preferably where a polymerization ratio is 30% or more and 80% or less, the polymerization conditions are preferably such that the polymerization rate is more than 3.5%/hr and 15.0%/hr or less, and the standard deviation of the polymerization rate (slope) every predetermined time is 10%/hr or less.

In the present embodiment, it is possible to implement the polymerization conditions by the following steps.

The average polymerization rate from the point when the polymerization ratio is more than 20% to the point when the polymerization ratio is 90% is determined by selecting from the range of more than 3.5%/hr and 15.0%/hr or less, calculating a plurality of polymerization rates every predetermined time in the time when the polymerization ratio is more than 20% to 90%, calculating the standard deviation, which is the positive square root of the variance of the plurality of polymerization rates and the average polymerization rate, and setting the calculated standard deviation to 10%/hr or less.

It is possible to calculate the average polymerization rate from when the polymerization ratio is more than 20% to when the polymerization ratio is 90% by (90%−20%)/(t4−t3) when the time when the polymerization ratio is more than 20% is t3 (hr) and the time when the polymerization ratio is 90% is t4 (hr).

Examples of a typical polymerization method when manufacturing the optical material (for example, a plastic lens) of the present invention include cast polymerization. That is, the polymerizable composition of the present invention is injected between a pair of molds held by a gasket, tape, or the like. At this time, the polymerizable composition may be mixed with a resin modifier as necessary, and a depressurizing process such as a defoaming operation, or an operation such as filter filtration may be performed in advance. Next, curing is performed by a method of leaving the pair of molds at room temperature or by heating the pair of molds in an apparatus able to perform heating, such as an oven, or in water and the resin can be taken out.

From the viewpoint of productivity, the heating and polymerization conditions of the composition of the present invention injected into a pair of molds are performed at a temperature of approximately −50° to 200° C. over 0.1 to 150 hours.

By calculating the polymerization temperature for each polymerization time based on the polymerization conditions, the polymerization ratio of the optical material is increased, it is possible to suppress variations in the temperature distribution during the polymerization of the polymerizable composition and to suppress the generation of optical distortion and striae in the optical material as a result.

In particular, even in an optical material such as a lens having a large layer thickness in which optical distortion and striae are easily generated, it is possible to effectively suppress the generation of optical distortion and striae. A lens (thick lens) having a large layer thickness means a lens having a center thickness in the range of approximately 4 to 25 mm.

In the storage unit 100, desired polymerization conditions in a range of a polymerization ratio of 0% or more and less than 100% are stored in advance by a user. Specifically, the storage unit 100 stores a desired polymerization rate and standard deviation of the polymerization rate in advance. It is also possible to directly input to the polymerization temperature calculating unit 180 from an input unit (not shown). In addition, a desired reaction time from when the polymerization ratio exceeds 20% to when the polymerization ratio reaches 90% may be stored in advance by the user in the storage unit 100.

The polymerization temperature calculating unit 180 acquires the reaction rate coefficient from the reaction rate coefficient calculating unit 160 and acquires the desired polymerization conditions from the storage unit 100. The reaction rate coefficient is associated with the type of the polymerizable reactive compound, which includes the episulfide compound, and the polymerization temperature calculating unit 180 selects a first-order reaction rate equation or a second-order reaction rate equation based on the type of the polymerizable reactive compound. Then, the polymerization temperature calculating unit 180 performs a back-calculation using the selected reaction rate equation and calculates the polymerization temperature condition for each polymerization time, so as to satisfy the desired polymerization conditions acquired from the storage unit 100.

The polymerization temperature calculating unit 180 also acquires the polymerization ratio from the reaction rate coefficient calculating unit 160 and the polymerization temperature calculating unit 180 transmits the polymerization temperature conditions for each polymerization time and the polymerization ratio to be stored in the storage unit 100.

The polymerization temperature calculating unit 180 may be configured so as to be able to output the polymerization temperature and the polymerization ratio for each polymerization time to a monitor (not shown) or the like. Due to this, it is possible for the user to check the polymerization temperature and the polymerization ratio for each polymerization time and to carry out the polymerization reaction according to these conditions.

The optical material manufacturing device of the present embodiment is provided with the polymerization condition setting device described above. Specifically, the optical material manufacturing device of the present embodiment is provided with a heating unit for heating a composition which includes a polymerizable reactive compound including an episulfide compound, and a polymerization catalyst, the polymerization condition setting device 10 of the present embodiment, and a control unit for controlling the heating unit to heat the composition including a polymerizable reactive compound, which includes the episulfide compound, and a polymerization catalyst, based on polymerization temperature conditions obtained by the polymerization condition setting device 10.

The heating unit is an apparatus which is able to heat a mold filled with a composition and examples of heating furnaces include an electric furnace, a hot-air circulation furnace, an infrared oven, a microwave oven, and the like.

The control unit may be installed integrally with or separately from the heating furnace and may be provided with a means for measuring a heat value (for example, measurement of the temperature distribution in the oven, the outer surface temperature of the mold, the inner surface temperature of the mold, and the temperature in the polymerizing step until the composition is cured) and a monitor. Furthermore, the control unit is configured so as to be able to access the storage unit 100 of the polymerization condition setting device 10 and to be able to monitor the temperature of the heating unit.

After the start of the polymerization, the control unit monitors the temperature of the polymerizable composition, compares the temperature with the polymerization temperature conditions for each polymerization time obtained from the storage unit 100, and controls the heating unit based on the polymerization temperature conditions. The optical material manufacturing device of the present embodiment is able to suitably execute the method for manufacturing an optical material of the present embodiment, to suppress the generation of optical distortion and striae, and to obtain an optical material excellent in appearance.

That is, the method for manufacturing the optical material of the present embodiment includes a step of calculating the polymerization temperature condition every predetermined time in the polymerization time according to the method for setting polymerization condition (step (A)) of the present embodiment, a step of injecting a composition which includes a polymerizable reactive compound including an episulfide compound, and a polymerization catalyst into a mold, and a step of polymerizing and curing the composition so as to satisfy the calculated polymerization temperature condition for each polymerization time.

Embodiments of the present invention were described above with reference to the drawings; however, the above are merely examples of the present invention and it is also possible to adopt various configurations other than the above.

EXAMPLES

A more detailed description will be given of the present invention with reference to Examples, but the present invention is not limited thereto.

Optical distortion and striae were measured and evaluated by the following methods.
(Optical Distortion)

Using a strain scope, the obtained plastic lens was visually observed, and the optical distortion of the plastic lens was evaluated in the following three stages.

No optical distortion: good

Slight optical distortion is observed: mediocre

Large optical distortion: poor
(Striae)

The obtained plastic lens was visually observed by the schlieren method and the striae of the plastic lens were evaluated in the following three stages.

No striae: good

Slight striae are observed: mediocre

A large number of striae: poor

The following components were used in the Examples and Comparative Examples.
<Ultraviolet Absorber>
TINUVIN PS: benzotriazole-based UV absorber manufactured by BASF Example 1

To 500.0 parts by weight of bis(2,3-epithiopropyl) disulfide, 5.5 parts by weight of UV absorber TINUVIN PS, 0.063 parts by weight of N, N-dimethylcyclohexylamine as a polymerization catalyst, and 0.5 parts by weight of N,N-dicyclohexylmethylamine as a polymerization catalyst were added, and the mixture was rapidly stirred and dissolved.

Furthermore, 47.2 parts by weight of a thiol composition including 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane were added thereto and the mixture was rapidly mixed and stirred at 15° C. Approximately 0.5 g of the stirred solution was placed as two samples (for two test temperatures) in sample bottles and rapidly depressurized and degassed by a vacuum pump. The reduced pressure was returned to atmospheric pressure. Using a differential scanning calorimeter, the heat value of the sample immediately after the preparation was measured as a reaction time of zero hours. The sample bottles of the two samples were subjected to nitrogen substitution and analysis was performed by a differential scanning calorimeter three times at 20° C. for every elapsed time (after 0 hours, after 6 hours, and after 24 hours) and three times at 60° C. for every elapsed time (after 0 hours, after 1 hour, and after 3 hours) to obtain heat values.

Heat value after 0 hours at 20° C.: 664.2 (J/g)

Heat value after 6 hours at 20° C.: 611.7 (J/g)

Heat value after 24 hours at 20° C.: 515.1 (J/g)

Heat value after 0 hours at 60° C.: 664.2 (J/g)

Heat value after 1 hour at 60° C.: 600.3 (J/g)

Heat value after 3 hours at 60° C.: 513.1 (J/g)

The heat values described above were directly input and stored in the storage unit 100 and the polymerization temperature conditions were calculated by the polymerization condition analysis apparatus 10 of the present embodiment.

In the remaining functional group ratio calculating unit 140, results were obtained in which at 20° C., the remaining functional group ratio immediately after mixing and stirring was 1.0000, the remaining functional group ratio after 6 hours was 0.9210, and the remaining functional group ratio after 24 hours was 0.7754, and, at 60° C., the remaining functional group ratio immediately after mixing and stirring was 1.0000, the remaining functional group ratio after 1 hour was 0.9037, and the remaining functional group ratio after 3 hours was 0.7725.

Figure 3:
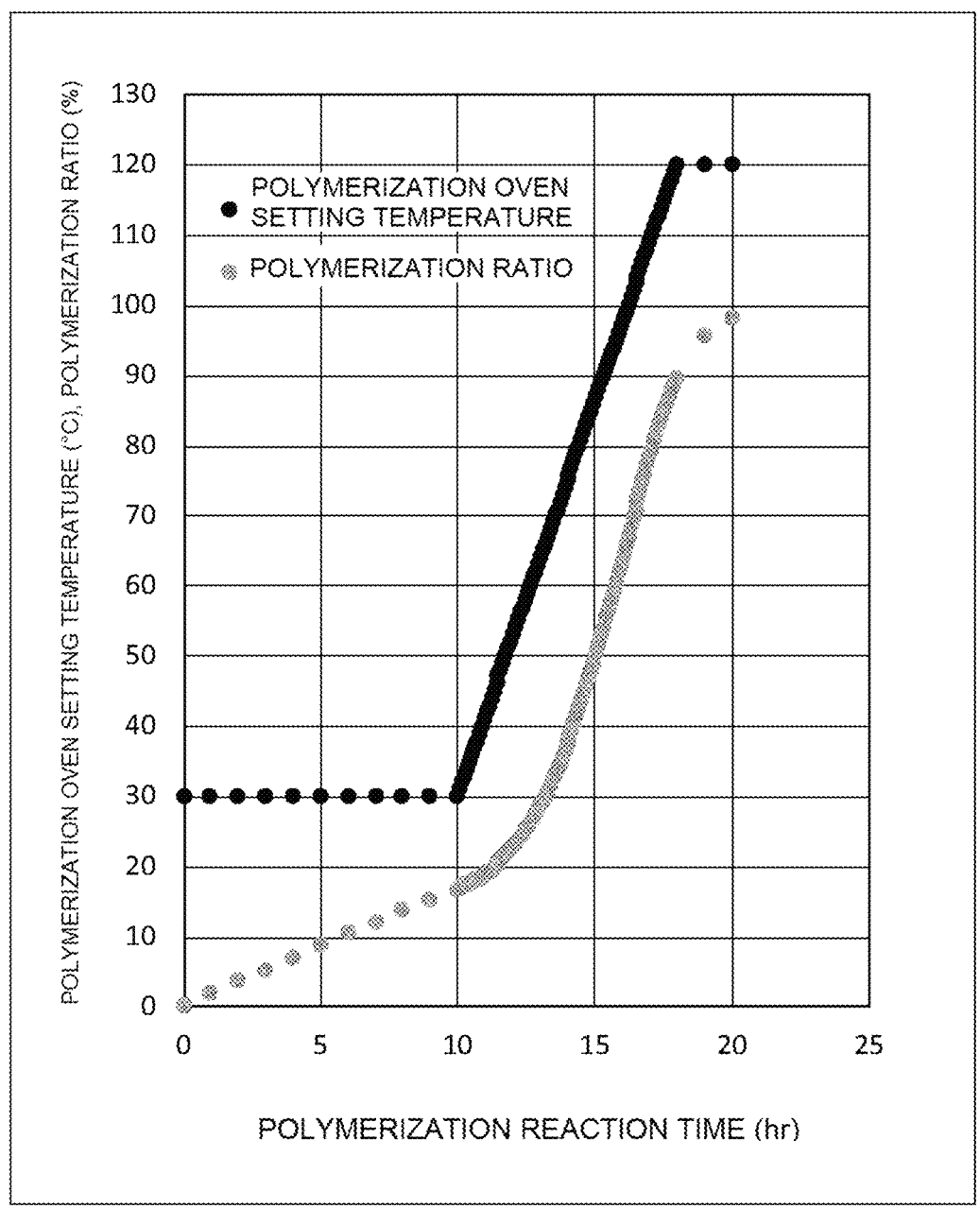
FIG. 3 is a chart in which a polymerization temperature condition for each polymerization time obtained by the method for setting polymerization condition, a polymerization time, and a polymerization ratio in Example 1 are plotted.

The reaction rate coefficient calculating unit 160 used a first-order reaction rate equation and the reaction rate coefficient, which is the slope of the regression line, was 0.0104 at 20° C. and 0.0850 at 60° C. In the storage unit 100, polymerization conditions were stored in which the slope (average polymerization rate) of the polymerization ratio from 0% to 20% was 1.71%/hr (20%–0%/11.7 hr), the standard deviation of the polymerization rate per hour was 0.14%/hr, the slope (polymerization rate) of the polymerization ratio from 30% to 80% was 12.43% (average value), and the standard deviation of the polymerization rate per hour was 2.51%/hr. The polymerization temperature calculating unit 180 accessed the polymerization conditions stored in the storage unit 100 and calculated the polymerization ratio and the polymerization temperature conditions for every polymerization time using an Arrhenius equation, based on the reaction rate coefficient for each polymerization time shown in Table 1 below. FIG. 3 shows a chart in which polymerization temperature conditions for each polymerization time, a polymerization time, and a polymerization ratio, which are displayed on a monitor, are plotted.

TABLE 1

| Polymerization time | Reaction rate coefficient | Polymerization ratio (%) | Polymerization temperature (° C.) |
|---|---|---|---|
| 0 hours | 0.0184 | 0 | 30 |
| 1 hour | 0.0184 | 1.8 | 30 |
| 2 hours | 0.0184 | 3.6 | 30 |
| 3 hours | 0.0184 | 5.4 | 30 |
| 4 hours | 0.0184 | 7.1 | 30 |
| 5 hours | 0.0184 | 8.8 | 30 |
| 6 hours | 0.0184 | 10.4 | 30 |
| 7 hours | 0.0184 | 12.1 | 30 |
| 8 hours | 0.0184 | 13.7 | 30 |
| 9 hours | 0.0184 | 15.2 | 30 |
| 10 hours | 0.0184 | 16.8 | 30 |
| 11 hours | 0.0336 | 18.9 | 41.2 |
| 12 hours | 0.0592 | 22.6 | 52.5 |
| 13 hours | 0.1003 | 28.5 | 63.8 |
| 14 hours | 0.1639 | 37.4 | 75 |
| 15 hours | 0.2597 | 49.4 | 86.2 |
| 16 hours | 0.4011 | 63.7 | 97.5 |
| 17 hours | 0.6038 | 78.1 | 108.8 |
| 18 hours | 0.8861 | 89.6 | 120 |
| 19 hours | 0.8861 | 95.7 | 120 |
| 20 hours | 0.8861 | 98.2 | 120 |

Example 2

Polymerization was carried out under the temperature conditions obtained in Example 1.

To 1000.0 parts by weight of bis(2,3-epithiopropyl) disulfide as a raw material, 11.0 parts by weight of UV absorber TINUVIN PS, 0.126 parts by weight of N,N-dimethylcyclohexylamine as a polymerization catalyst, and 1.0 part by weight of N,N-dicyclohexylmethylamine as a polymerization catalyst were added, and the mixture was rapidly stirred and dissolved. Furthermore, 94.4 parts by weight of a thiol composition including 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane were added thereto and the mixture was mixed and stirred at 15° C. Thereafter, filtration was carried out to purify the mixed solution and the solution was depressurized by a vacuum pump and degassed. This solution was cast in a glass mold to create 10 samples. The above was carried out in a mold shape of 081 mm, in which the front surface had 2 curves, the back surface had 4 curves, and the center thickness was thick at 10.0 mm.

Polymerization was performed by the optical material manufacturing device of the present embodiment. Based on the temperature conditions obtained in Example 1, the temperature of the polymerization oven was set and the temperature conditions were controlled. After the completion of the polymerization (polymerization ratio: 98.2%), a cured episulfide resin was obtained from the polymerization oven after cooling. After removing internal stress by an annealing process, the obtained resin was evaluated for optical distortion by a high-pressure mercury lamp and three-stage evaluation of striae was carried out, as a result, for 10 out of 10 samples, lenses were obtained in which optical distortion and striae were not observed (good in each evaluation) and which were extremely excellent for optical applications.

Example 3

Figure 4:
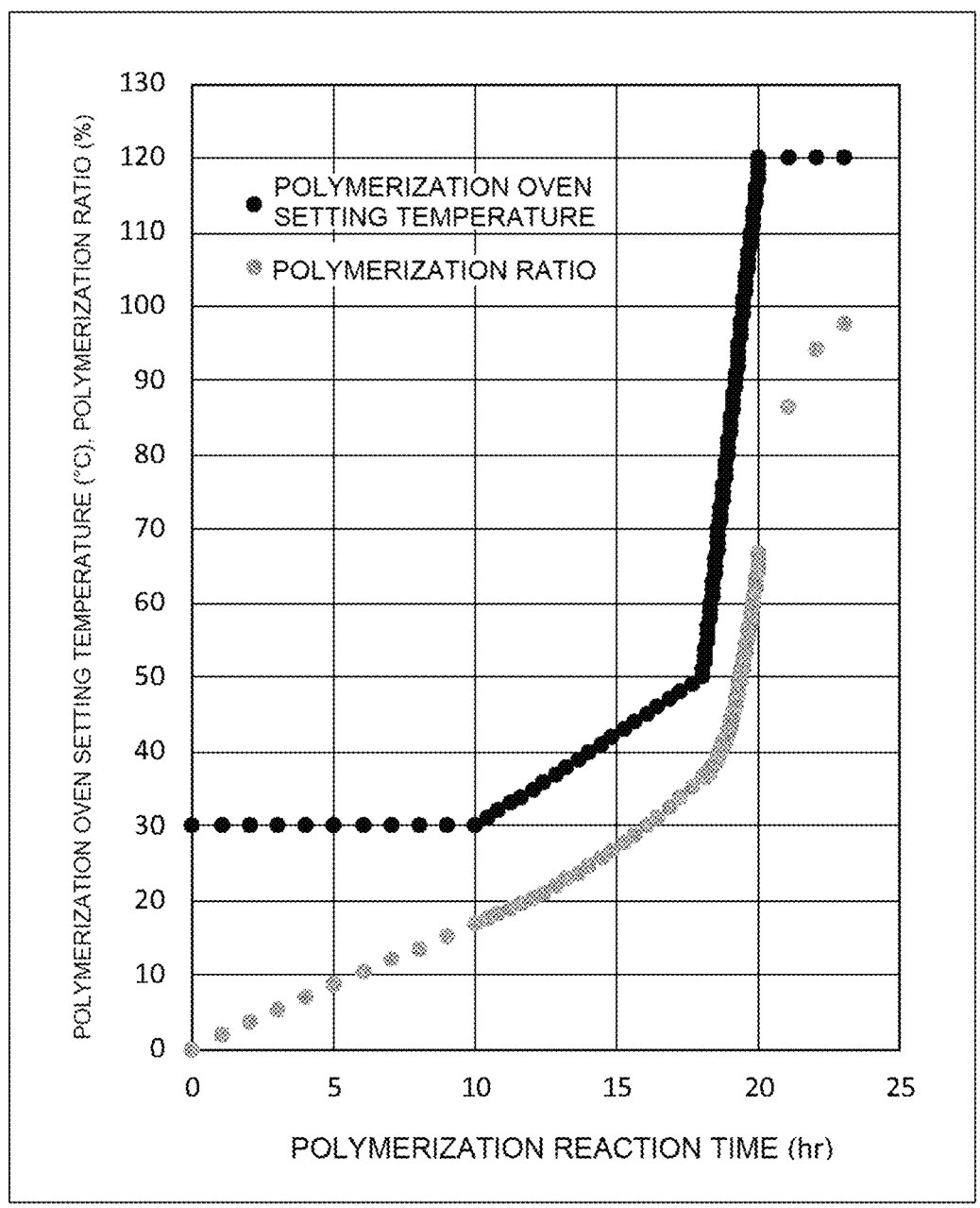
FIG. 4 is a chart in which a polymerization temperature condition for each polymerization time obtained by the method for setting polymerization condition, a polymerization time, and a polymerization ratio in Example 3 are plotted.

In the same manner as in Example 1, except that the slope (polymerization rate) of the polymerization ratio from 0% to 20% was 1.69%/hr (average value), the standard deviation of the polymerization rate per hour was 0.10%/hr, the polymerization rate when the polymerization ratio was 30 to 80% was 11.25%/hr (average value), and the standard deviation of the polymerization rate per hour was 8.23%/hr, the polymerization temperature calculating unit 180 accessed the polymerization conditions stored in the storage unit 100 and calculated the polymerization ratio and the polymerization temperature conditions for every polymerization time using an Arrhenius equation, based on the reaction rate coefficient for each polymerization time. FIG. 4 shows a chart in which polymerization temperature conditions for each polymerization time, a polymerization time, and a polymerization ratio, which are displayed on a monitor, are plotted.

Example 4

Polymerization was carried out under the temperature conditions obtained in Example 3.

To 1000.0 parts by weight of bis(2,3-epithiopropyl) disulfide as a raw material, 11.0 parts by weight of UV absorber TINUVIN PS, 0.126 parts by weight of N,N-dimethylcyclohexylamine as a polymerization catalyst, and 1.0 part by weight of N, N-dicyclohexylmethylamine as a polymerization catalyst were added, and the mixture was rapidly stirred and dissolved. Furthermore, 94.4 parts by weight of a thiol composition including 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane were added thereto and the mixture was mixed and stirred at 15° C. Thereafter, filtration was carried out to purify the mixed solution and the solution was depressurized by a vacuum pump and degassed. This solution was cast in a glass mold to create 10 samples. The above was carried out in a mold shape of 081 mm, in which the front surface had 2 curves, the back surface had 4 curves, and the center thickness was thick at 10.0 mm.

Polymerization was performed by the optical material manufacturing device of the present embodiment. Based on the temperature conditions obtained in Example 3, the temperature of the polymerization oven was set and the temperature conditions were controlled. After the completion of the polymerization (polymerization ratio: 98.2%), a cured episulfide resin was obtained from the polymerization oven after cooling. After removing internal stress by an annealing treatment, the obtained resin was evaluated for optical distortion by a high-pressure mercury lamp and three-stage evaluation of striae was carried out, as a result, for 10 out of 10 samples, lenses were obtained in which optical distortion and striae were not observed (good in each evaluation) and which were extremely excellent for optical applications.

Example 5

In 809.7 parts by weight of bis(2,3-epithiopropyl) sulfide, 27.0 parts by weight of sulfur powder was mixed at 5° C. to 15° C., 0.43 parts by weight of a diluted solution in which 0.022 parts by weight of 1,2-dimethylimidazole as a vulcanization catalyst was diluted with 20 times of toluene was added thereto and the mixture was stirred at 5° C. to 15° C. for 1 hour. Hydrogen sulfide generated during vulcanization was removed by substituting the gas phase portion of the mixed solution with nitrogen to obtain a vulcanized solution.

To the vulcanized solution, 161.9 parts by weight of bis(2-mercaptoethyl) sulfide as a thiol and 1.3 parts by weight of tetra-n-butylphosphonium bromide as a polymerization catalyst were added, and the mixture was rapidly stirred and dissolved. Approximately 0.5 g of the solution was placed in sample bottles and two samples (for two test temperatures) were substituted with nitrogen. In order to investigate the reaction rate of the vulcanizate and thiol of the sample immediately after the preparation, the heat value was measured using a differential scanning calorimeter as a reaction time of zero hours. The sample bottles of the two samples were further subjected to nitrogen substitution, heat values were obtained by performing analysis by a differential scanning calorimeter two times at 20° C. for every elapsed time (after 0 hours and after 3 hours), and three times at 40° C. for every elapsed time (after 0 hours, after 0.5 hours, and after 1 hour).

Heat value after 0 hours at 20° C.: 524.2 (J/g)
Heat value after 3 hours at 20° C.: 514.8 (J/g)
Heat value after 0 hours at 40° C.: 524.2 (J/g)
Heat value after 0.5 hours at 40° C.: 476.5 (J/g)
Heat value after 1 hour at 40° C.: 432.5 (J/g)

The heat values described above were directly input and stored in the storage unit 100 and the polymerization temperature conditions were calculated by the polymerization condition analysis apparatus 10 of the present embodiment.

In the remaining functional group ratio calculating unit 140, results were obtained in which at 20° C., the remaining functional group ratio immediately after mixing and stirring was 1.0000, and the remaining functional group ratio after 3 hours was 0.9821, and, at 40° C., the remaining functional group ratio immediately after mixing and stirring was 1.0000, the remaining functional group ratio after 0.5 hours was 0.9090, and the remaining functional group ratio after 1 hour was 0.8251.

The reaction rate coefficient calculating unit 160 used a first-order reaction rate equation and the reaction rate coefficient, which is the slope of the regression line, was 0.0060 at 20° C. and 0.1922 at 40° C.

Figure 5:
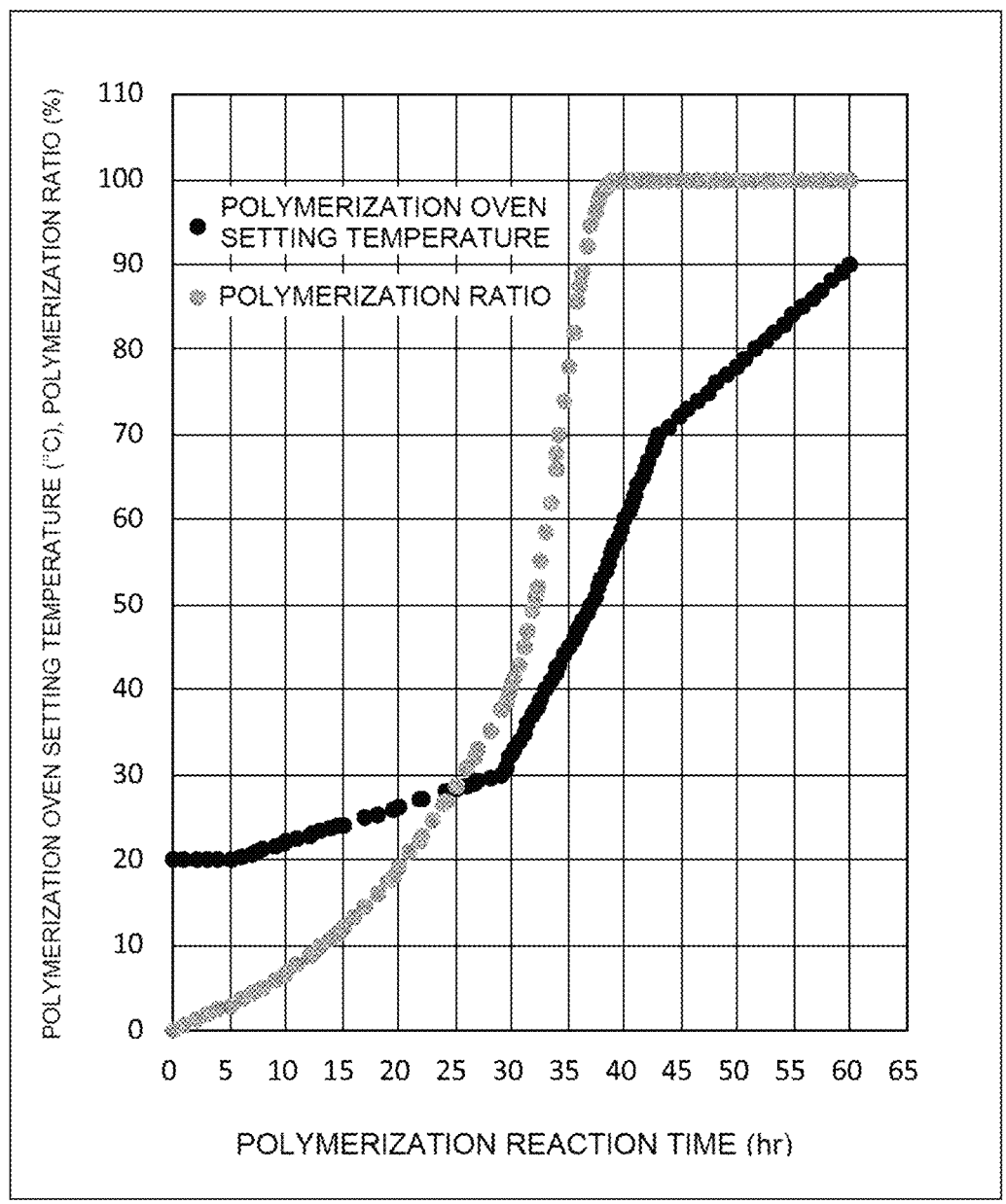
FIG. 5 is a chart in which a polymerization temperature condition for each polymerization time obtained by the method for setting polymerization condition, a polymerization time, and a polymerization ratio in Example 5 are plotted.

In the storage unit 100, polymerization conditions were stored in which the slope (polymerization rate) of the polymerization ratio from 0% to 20% was 0.95%/hr (average value), the standard deviation of the polymerization rate per hour was 0.34%/hr, the polymerization rate at a polymerization ratio from 30 to 80% was 5.92%/hr (average value), and the standard deviation of the polymerization rate per hour was 2.80%/hr. The polymerization temperature calculating unit 180 accessed the polymerization conditions stored in the storage unit 100 and calculated the polymerization ratio and the polymerization temperature conditions for every polymerization time using an Arrhenius equation, based on the reaction rate coefficient for each polymerization time. FIG. 5 shows a chart in which polymerization temperature conditions for each polymerization time, a polymerization time, and a polymerization ratio, which are displayed on a monitor, are plotted.

Example 6

Polymerization was performed under the temperature conditions obtained in Example 5.

In 809.7 parts by weight of bis(2,3-epithiopropyl) sulfide as a raw material, 27.0 parts by weight of sulfur powder was mixed at 5° C. to 15° C., 0.43 parts by weight of a diluted solution in which 0.022 parts by weight of 1,2-dimethylimidazole as a vulcanization catalyst was diluted with 20 times of toluene was added thereto and the mixture was stirred at 5° C. to 15° C. for 1 hour. Hydrogen sulfide generated during vulcanization was removed by substituting the gas phase portion of the mixed solution with nitrogen to obtain a vulcanized solution.

To the vulcanized solution, 161.9 parts by weight of bis(2-mercaptoethyl) sulfide and 1.3 parts by weight of tetra-n-butylphosphonium bromide as a polymerization catalyst were added, and the mixture was stirred and dissolved. Thereafter, filtration was carried out to purify the mixed solution and the mixture was degassed while stirring slowly under normal pressure until bubbles escaped upward. This solution was cast in a glass mold to create 10 samples. The above was carried out in a mold shape of 081 mm, in which the front surface had 2 curves, the back surface had 4 curves, and the center thickness was thick at 10.0 mm.

Polymerization was performed by the optical material manufacturing device of the present embodiment. Based on the temperature conditions obtained in Example 5, the temperature of the polymerization oven was set and the temperature conditions were controlled. After the completion of the polymerization (polymerization ratio: 99.9% or more), a cured episulfide resin was obtained from the polymerization oven after cooling. After removing internal stress by an annealing treatment, the obtained resin was evaluated for optical distortion by a high-pressure mercury lamp and three-stage evaluation of striae was carried out, as a result, for 10 out of 10 samples, lenses were obtained in which optical distortion and striae were not observed (good in each evaluation) and which were extremely excellent for optical applications.

Example 7

Figure 6:
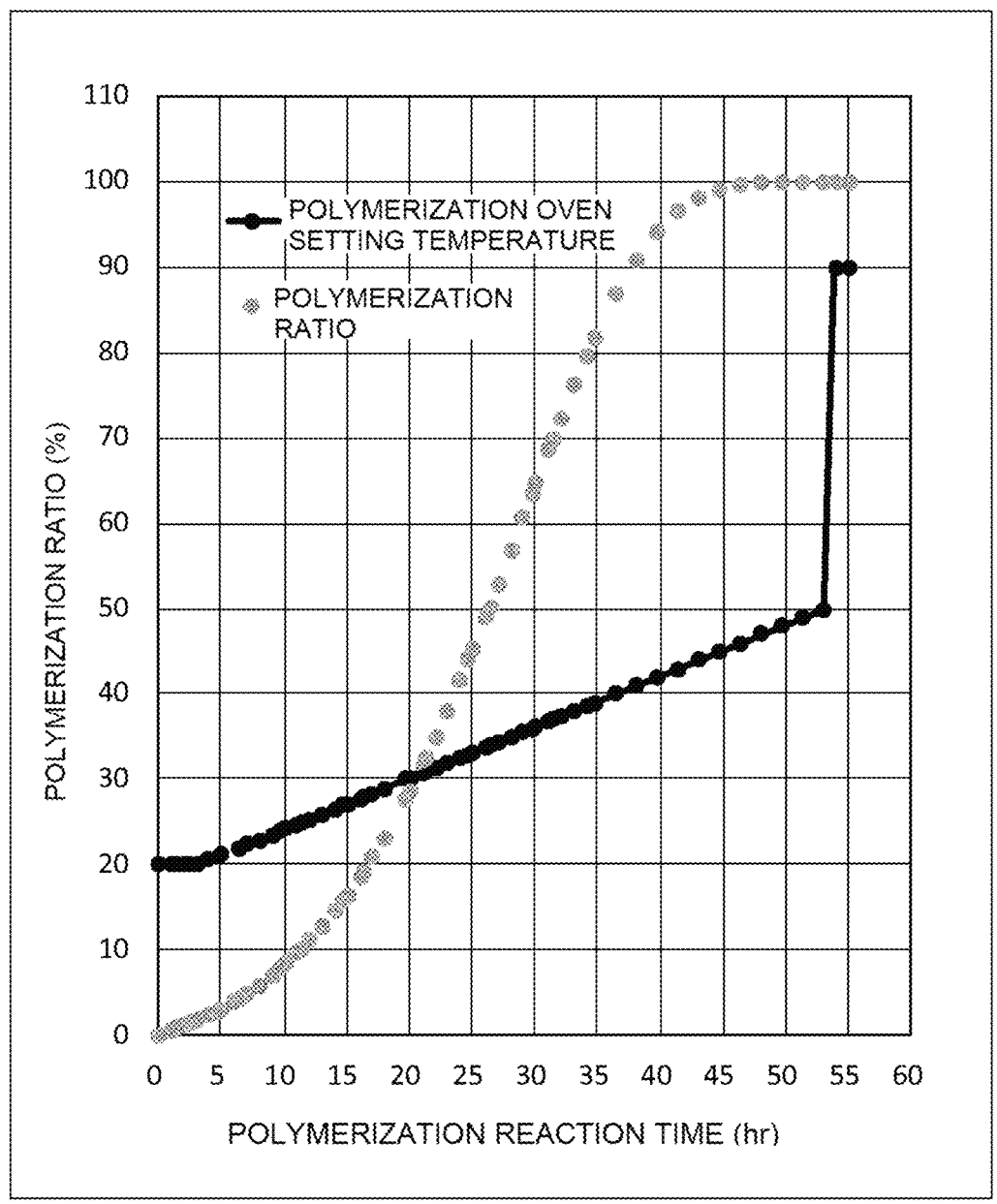
FIG. 6 is a chart in which a polymerization temperature condition for each polymerization time obtained by the method for setting polymerization condition, a polymerization time, and a polymerization ratio in Example 7 are plotted.

In the same manner as in Example 5, except that the slope (polymerization rate) of the polymerization ratio from 0% to 20% was 1.16%/hr (average value), the standard deviation of the polymerization rate per hour was 0.49%/hr, the polymerization rate when the polymerization ratio was 30 to 80% was 3.79%/hr, and the standard deviation of the polymerization rate per hour was 1.21%/hr, the polymerization temperature calculating unit 180 accessed the polymerization conditions stored in the storage unit 100 and calculated the polymerization ratio and the polymerization temperature conditions for every polymerization time using an Arrhenius equation, based on the reaction rate coefficient for each polymerization time. FIG. 6 shows a chart in which polymerization temperature conditions for each polymerization time, a polymerization time, and a polymerization ratio, which are displayed on a monitor, are plotted.

Example 8

Polymerization was performed under the temperature conditions obtained in Example 7.

In 809.7 parts by weight of bis(2,3-epithiopropyl) sulfide as a raw material, 27.0 parts by weight of sulfur powder was mixed at 5° C. to 15° C., 0.43 parts by weight of a diluted solution in which 0.022 parts by weight of 1,2-dimethylimidazole as a vulcanization catalyst was diluted with 20 times of toluene was added thereto and the mixture was stirred at 5° C. to 15° C. for 1 hour. Hydrogen sulfide generated during vulcanization was removed by substituting the gas phase portion of the mixed solution with nitrogen to obtain a vulcanized solution.

To the vulcanized solution, 161.9 parts by weight of bis(2-mercaptoethyl) sulfide and 1.3 parts by weight of tetra-n-butylphosphonium bromide as a polymerization catalyst were added, and the mixture was stirred and dissolved. Thereafter, filtration was carried out to purify the mixed solution and the mixture was degassed while stirring slowly under normal pressure until bubbles escaped upward. This solution was cast in a glass mold to create 10 samples. The above was carried out in a mold shape of 081 mm, in which the front surface had 2 curves, the back surface had 4 curves, and the center thickness was thick at 10.0 mm.

Polymerization was performed by the optical material manufacturing device of the present embodiment. Based on the temperature conditions obtained in Example 7, the temperature of the polymerization oven was set and the temperature conditions were controlled. After the completion of the polymerization (polymerization ratio: 99.9% or more), a cured episulfide resin was obtained from the polymerization oven after cooling. After removing internal stress by an annealing treatment, the obtained resin was evaluated for optical distortion by a high-pressure mercury lamp and three-stage evaluation of striae was carried out, as a result, for 10 out of 10 samples, lenses were obtained in which optical distortion and striae were not observed (good in each evaluation) and which were extremely excellent for optical applications.

Comparative Example 1

Figure 7:
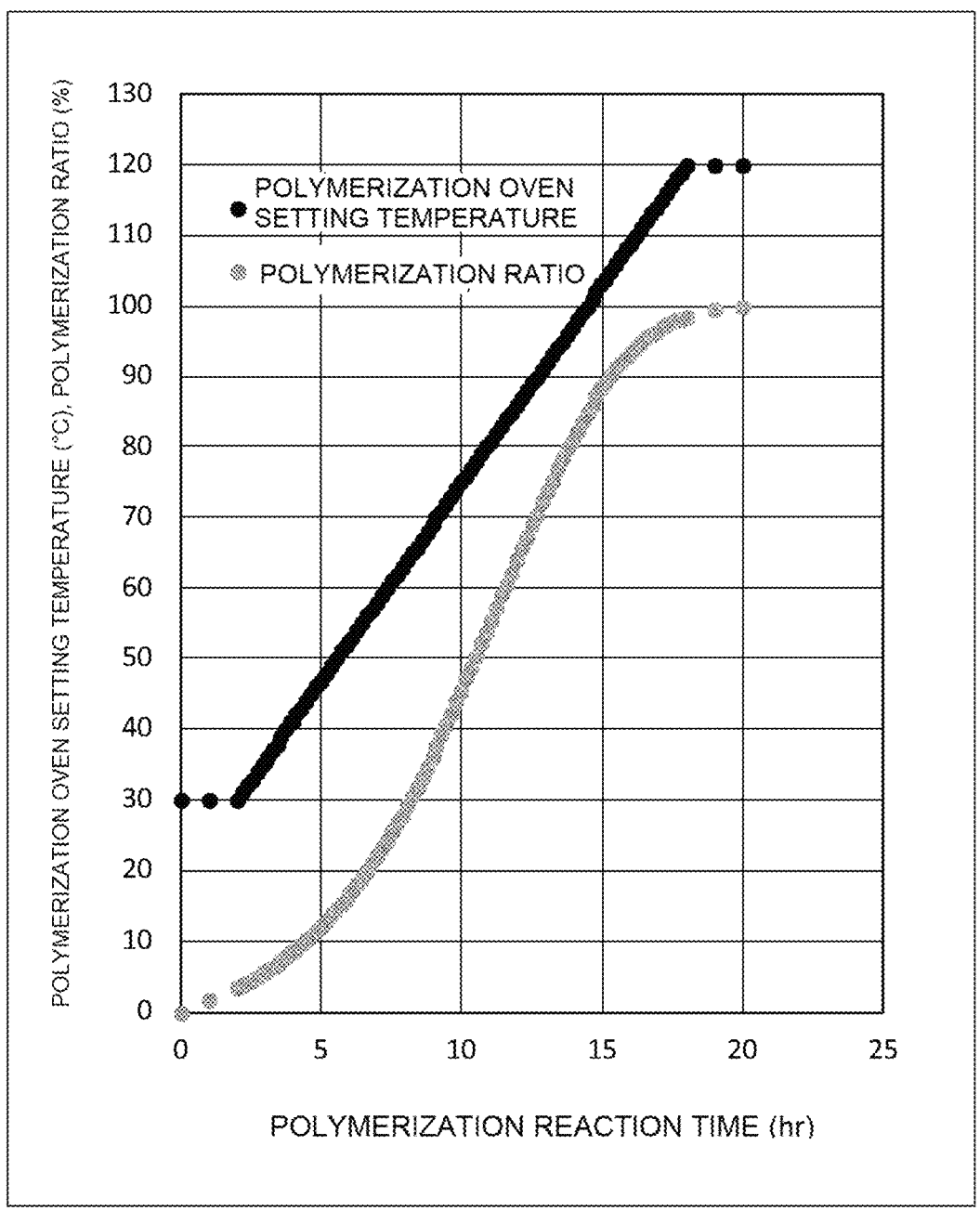
FIG. 7 is a chart in which a polymerization temperature condition for each polymerization time, a polymerization time, and a polymerization ratio in Comparative Example 1 are plotted.

In the same manner as in Example 1, except that the slope (polymerization rate) of the polymerization ratio from 0% to 20% was 3.16%/hr (average value), the standard deviation of the polymerization rate per hour of the polymerization ratio was 1.33%/hr, the polymerization rate when the polymerization ratio was 30 to 80% was 8.94%/hr (average value), and the standard deviation of the polymerization rate per hour was 0.79%/hr, the polymerization temperature calculating unit 180 accessed the polymerization conditions stored in the storage unit 100 and calculated the polymerization ratio and the polymerization temperature conditions for every polymerization time using an Arrhenius equation, based on the reaction rate coefficient for each polymerization time. FIG. 7 shows a chart in which polymerization temperature conditions for each polymerization time, a polymerization time, and a polymerization ratio, which are displayed on a monitor, are plotted. Polymerization was carried out under the polymerization temperature conditions shown in FIG. 7.

To 1000.0 parts by weight of bis(2,3-epithiopropyl) disulfide as a raw material, 11.0 parts by weight of UV absorber TINUVIN PS, 0.126 parts by weight of N,N-dimethylcyclohexylamine as a polymerization catalyst, and 1.0 part by weight of N,N-dicyclohexylmethylamine as a polymerization catalyst were added, and the mixture was rapidly stirred and dissolved. Furthermore, 94.4 parts by weight of a thiol composition including 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane were added thereto and the mixture was mixed and stirred at 15° C. Thereafter, filtration was carried out to purify the mixed solution and the solution was depressurized by a vacuum pump and degassed. This solution was cast in a glass mold to create 10 samples. The above was carried out in a mold shape of 081 mm, in which the front surface had 2 curves, the back surface had 4 curves, and the center thickness was thick at 10.0 mm.

Polymerization was performed by the optical material manufacturing device of the present embodiment. Based on the temperature conditions shown in FIG. 7, the temperature of the polymerization oven was set and the temperature conditions were controlled. After the polymerization was completed (polymerization ratio: 99.8%), a cured episulfide resin was obtained from the polymerization oven after cooling. After removing internal stress by an annealing process, the obtained resin was evaluated for optical distortion by a high-pressure mercury lamp and three-stage evaluation of striae was carried out, as a result, for 10 out of 10 samples, optical distortion and striae were generated (poor in all evaluations) and use was not possible for an optical application.

Comparative Example 2

Figure 8:
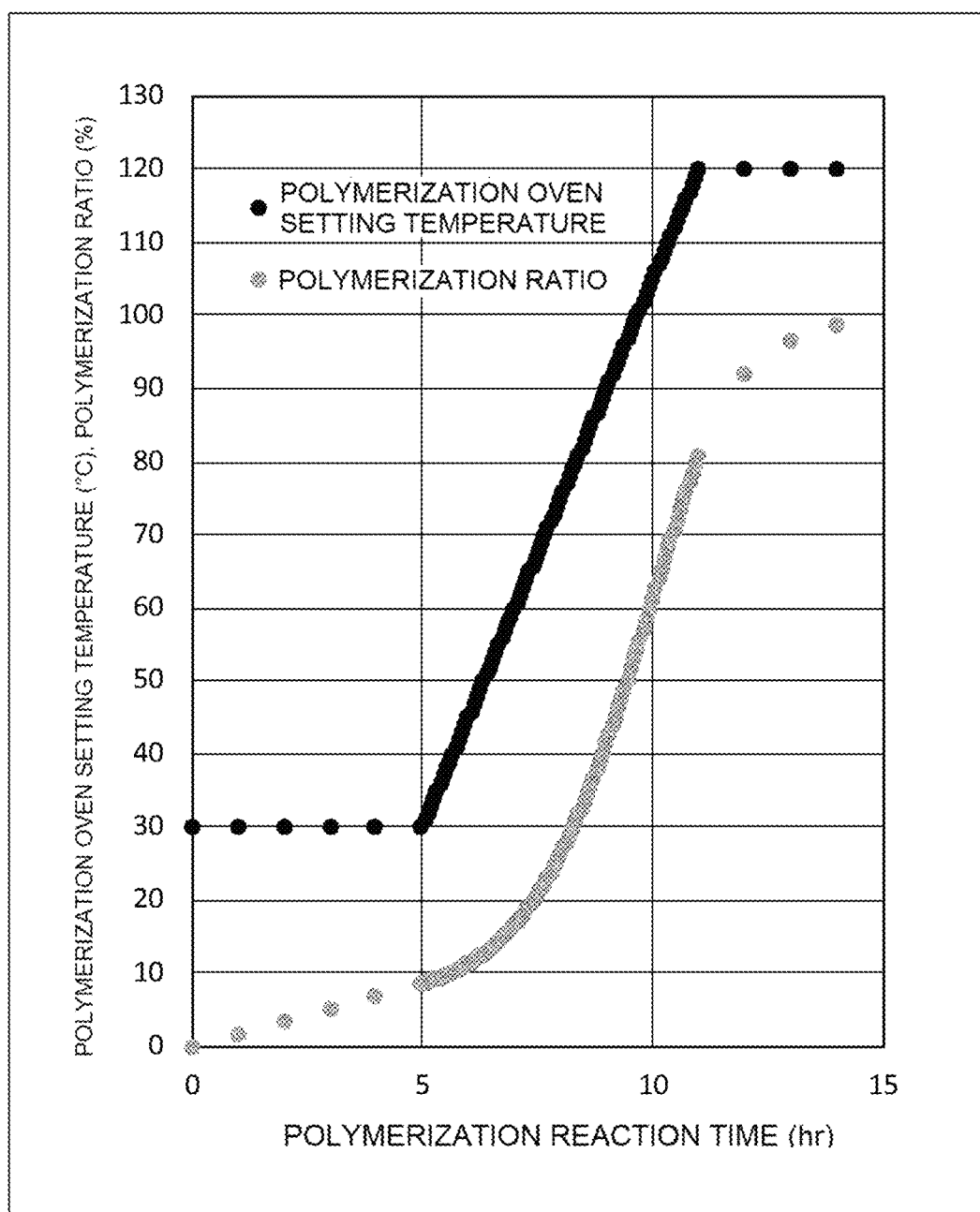
FIG. 8 is a chart in which a polymerization temperature condition for each polymerization time, a polymerization time, and a polymerization ratio in Comparative Example 2 are plotted.

In the same manner as in Example 6, except that the slope (polymerization rate) of the polymerization ratio from 0% to 20% was 2.38%/hr (average value), the standard deviation of the polymerization rate per hour of the polymerization ratio was 1.23%/hr, the polymerization rate when the polymerization ratio was 30 to 80% was 16.72%/hr (average value), and the standard deviation of the polymerization rate per hour was 3.16%/hr, the polymerization temperature calculating unit 180 accessed the polymerization conditions stored in the storage unit 100 and calculated the polymerization ratio and the polymerization temperature conditions for every polymerization time using an Arrhenius equation, based on the reaction rate coefficient for each polymerization time. FIG. 8 shows a chart in which polymerization temperature conditions for each polymerization time, a polymerization time, and a polymerization ratio, which are displayed on a monitor, are plotted. Polymerization was carried out under the polymerization temperature conditions shown in FIG. 8.

In 809.7 parts by weight of bis(2,3-epithiopropyl)disulfide as a raw material, 27.0 parts by weight of sulfur powder was mixed at 5° C. to 15° C., 0.43 parts by weight of a vulcanized solvent diluted solution in which 0.022 parts by weight of 1,2-dimethylimidazole as a vulcanization catalyst was diluted with 20 times of toluene was added thereto and the mixture was stirred at 5° C. to 15° C. for 1 hour. Hydrogen sulfide generated during vulcanization was removed by substituting the gas phase portion of the mixed solution with nitrogen to obtain a vulcanized solution.

To the vulcanized solution, 161.9 parts by weight of bis(2-mercaptoethyl) sulfide as a thiol and 1.3 parts by weight of tetra-n-butylphosphonium bromide as a polymerization catalyst were added, and the mixture was stirred and dissolved. Thereafter, filtration was carried out to purify the mixed solution and the mixture was degassed while stirring slowly under normal pressure until bubbles escaped upward. This solution was cast in a glass mold to create 10 samples. The above was carried out in a mold shape of 081 mm, in which the front surface had 2 curves, the back surface had 4 curves, and the center thickness was thick at 10.0 mm.

Polymerization was performed by the optical material manufacturing device of the present embodiment. Based on the temperature conditions shown in FIG. 8, the temperature of the polymerization oven was set and the temperature conditions were controlled. After the polymerization was completed (polymerization ratio: 99.9% or more), a cured episulfide resin was obtained from the polymerization oven after cooling. After removing internal stress by an annealing treatment, the obtained resin was evaluated for optical distortion by a high-pressure mercury lamp and three-stage evaluation of striae was carried out, as a result, for 10 out of 10 samples, optical distortion and striae were generated (poor in all evaluations) and use was not possible for an optical application.

Comparative Example 3

Figure 9:
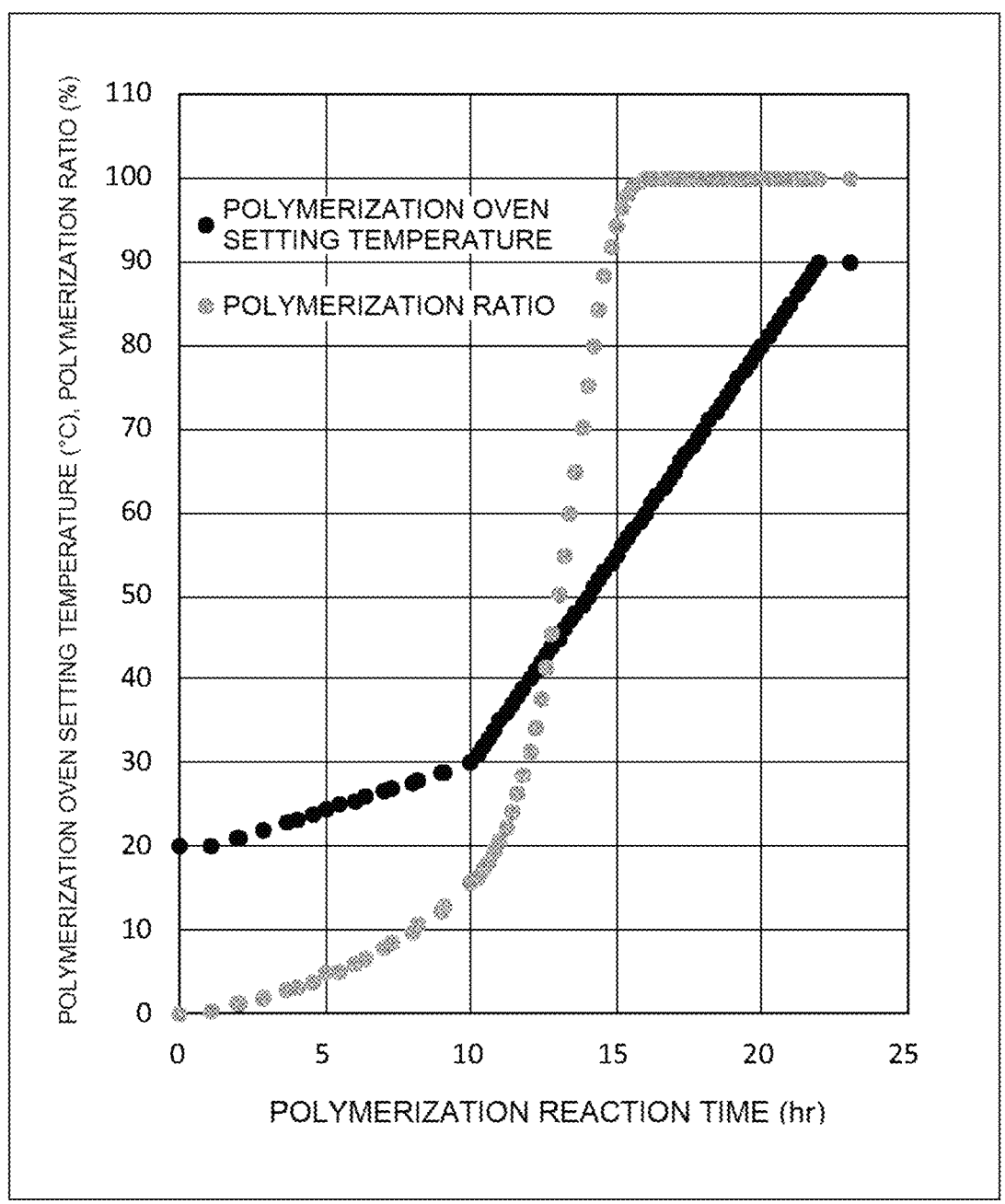
FIG. 9 is a chart in which a polymerization temperature condition for each polymerization time, a polymerization time, and a polymerization ratio in Comparative Example 3 are plotted.

In the same manner as in Example 6, except that the slope (polymerization rate) of the polymerization ratio from 0% to 20% was 2.08%/hr (average value), the standard deviation of the polymerization rate per hour of the polymerization ratio was 1.27%/hr, and the polymerization rate when the polymerization ratio was 30 to 80% was 21.90%/hr (average value), and the standard deviation of the polymerization rate per hour was 3.16%/hr, the polymerization temperature calculating unit 180 accessed the polymerization conditions stored in the storage unit 100 and calculated the polymerization ratio and the polymerization temperature conditions for every polymerization time using an Arrhenius equation, based on the reaction rate coefficient for each polymerization time. FIG. 9 shows a chart in which polymerization temperature conditions for each polymerization time, a polymerization time, and a polymerization ratio, which are displayed on a monitor, are plotted. Polymerization was carried out under the polymerization temperature conditions shown in FIG. 9.

In 809.7 parts by weight of bis(2,3-epithiopropyl) sulfide as a raw material, 27.0 parts by weight of sulfur powder was mixed at 5° C. to 15° C., 0.43 parts by weight of a diluted solution in which 0.022 parts by weight of 1,2-dimethylimidazole as a vulcanization catalyst was diluted with 20 times of toluene was added thereto and the mixture was stirred at 5° C. to 15° C. for 1 hour. Hydrogen sulfide generated during vulcanization was removed by substituting the gas phase portion of the mixed solution with nitrogen to obtain a vulcanized solution.

To the vulcanized solution, 161.9 parts by weight of bis(2-mercaptoethyl) sulfide and 1.3 parts by weight of tetra-n-butylphosphonium bromide as a polymerization catalyst were added, and the mixture was stirred and dissolved. Thereafter, filtration was carried out to purify the mixed solution and the mixture was degassed while stirring slowly under normal pressure until bubbles escaped upward. This solution was cast in a glass mold to create 10 samples. The above was carried out in a mold shape of 081 mm, in which the front surface had 2 curves, the back surface had 4 curves, and the center thickness was thick at 10.0 mm.

Polymerization was performed by the optical material manufacturing device of the present embodiment. Based on the temperature conditions shown in FIG. 9, the temperature of the polymerization oven was set and the temperature conditions were controlled. After the polymerization was completed (polymerization ratio: 99.9% or more), a cured episulfide resin was obtained from the polymerization oven after cooling. After removing internal stress by an annealing treatment, the obtained resin was evaluated for optical distortion by a high-pressure mercury lamp and three-stage evaluation of striae was carried out, as a result, for 10 out of 10 samples, optical distortion and striae were generated (poor in all evaluations) and use was not possible for an optical application.

This application claims priority based on Japanese Patent Application No. 2018-138123 filed on Jul. 24, 2018, and incorporates all of the disclosure thereof.

The invention claimed is:

1. A method for setting polymerization condition, comprising:
   providing a composition including a polymerizable reactive compound including an episulfide compound, and a polymerization catalyst;
   a physical property acquiring step comprising:
      acquiring a physical property value a derived from a functional group,
      heating the composition and retaining heat at a plurality of predetermined temperatures, wherein the acquiring the physical property value a is conducted before the heating, and
      acquiring a physical property value b derived from a remaining functional group after maintaining each of the plurality of predetermined temperatures for predetermined times;
   a remaining functional group ratio calculating step of calculating a remaining functional group ratio from the physical property value a and the physical property value b;
   a reaction rate coefficient calculating step of calculating a reaction rate coefficient from the remaining functional group ratio based on a predetermined reaction rate equation stored in a storage unit;
   a polymerization temperature calculating step of back-calculating a plurality of polymerization temperatures at predetermined time intervals within a polymerization time based on the reaction rate equation, using the reaction rate coefficient, such that the following conditions are satisfied;
      wherein the conditions are comprised of selecting and determining an average polymerization rate from a range of more than 0%/hr and 3.0%/hr or less in a range of 0% or more and 20% or less of a conversion ratio,
      calculating multiple polymerization rates at predetermined time intervals within the time when the conversion ratio is in a range of 0% or more and 20% or less, and calculating a standard deviation by the positive square root of the variance of the multiple polymerization rates and the average polymerization rate, and satisfying 0.8%/hr or less of the calculated standard deviation.

2. The method for setting polymerization condition according to claim 1,
wherein the episulfide compound is represented by General Formula (1),

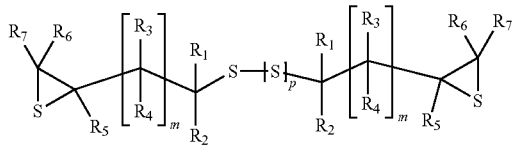

(1)

wherein in General Formula (1), $R_1$ to $R_7$ may be the same or different and represent a hydrogen atom, a linear or branched alkyl group having 1 or more and 10 or less carbon atoms, or a substituted or unsubstituted aryl group having 6 or more and 18 or less carbon atoms, m represents an integer of 0 or more and 2 or less, and p represents an integer of 0 or more and 4 or less.

3. The method for setting polymerization condition according to claim 1,
wherein a molar ratio of the functional group of the episulfide compound is 60 or more with respect to 100 by mole of a total of the functional group moles of the polymerizable reactive compound.

4. The method for setting polymerization condition according to claim 1,
wherein the polymerizable reactive compound includes at least one type selected from an active hydrogen compound, a polyiso(thio)cyanate compound, and an epoxy compound.

5. The method for setting polymerization condition according to claim 1,
wherein the physical property value a and the physical property value b are a heat value, a specific gravity, a weight average molecular weight, a number average molecular weight, a $^1$H-NMR spectral intensity, or a $^{13}$C-NMR spectral intensity.

6. The method for setting polymerization condition according to claim 1, further comprising:
a polymerization time setting step of selecting a reaction time, during which the polymerization ratio increases from more than 20% up to 90%, from 0.1 to 150 hours, after the polymerization temperature calculating step.

7. A method for manufacturing an optical material comprising:
conducting the method for setting polymerization condition according to claim 1;
a step of injecting a second composition which includes a polymerizable reactive compound including an episulfide compound, and a polymerization catalyst into a mold; and
a step of polymerizing and curing the second composition such that the calculated polymerization temperature conditions for each polymerization time are satisfied,
wherein the polymerization is performed under the plurality of polymerization temperatures at predetermined time intervals.

8. The method for manufacturing an optical material according to claim 7,
wherein the episulfide compound is represented by General Formula (1),

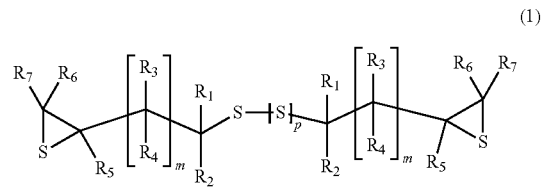

(1)

wherein in General Formula (1), $R_1$ to $R_7$ may be the same or different and represents a hydrogen atom, a linear or branched alkyl group having 1 or more and 10 or less carbon atoms, or a substituted or unsubstituted aryl group having 6 or more and 18 or less carbon atoms, m represents an integer of 0 or more and 2 or less, and p represents an integer of 0 or more and 4 or less.

9. The method for manufacturing an optical material according to claim 7,
wherein a molar ratio of the functional group of the episulfide compound is 60 or more with respect to 100 by mole of a total of the functional group moles of the polymerizable reactive compound.

10. The method for manufacturing an optical material according to claim 7,
wherein the polymerizable reactive compound includes at least one type selected from an active hydrogen compound and an epoxy compound.

11. The method for manufacturing an optical material according to claim 7, further comprising:
a polymerization time setting step of selecting a reaction time, during which the polymerization ratio increases from more than 20% up to 90%, from 0.1 to 150 hours, after the polymerization temperature calculating step.

12. A polymerization condition setting device comprising:
a physical property acquisition unit configured to:
heat a composition which includes a polymerizable reactive compound including an episulfide compound, and a polymerization catalyst, and maintain the composition at a predetermined temperature,
acquire a physical property value a derived from a functional group,
heat the composition and retain heat at a plurality of predetermined temperatures, wherein the acquiring the physical property value a is conducted before the heating, and
acquire a physical property value b derived from a remaining functional group after maintaining each of the plurality of predetermined temperatures for predetermined times;
a remaining functional group ratio calculating unit for calculating a remaining functional group ratio from the physical property value a and the physical property value b;
a reaction rate coefficient calculating unit for calculating a reaction rate coefficient from the remaining functional group ratio, based on a predetermined reaction rate equation stored in a storage unit; and
a polymerization temperature calculating unit for back-calculating a plurality of polymerization temperatures at predetermined time intervals within a polymerization time based on the reaction rate equation, using the reaction rate coefficient, such that the following conditions are satisfied;

wherein the conditions are comprised of selecting and determining an average polymerization rate from a range of more than 0%/hr and 3.0%/hr or less in a range of 0% or more and 20% or less of a polymerization ratio, calculating multiple polymerization rates at predetermined time intervals within the time when the polymerization rate is range of 0% or more and 20% or less, and calculating a standard deviation by the positive square root of the variance of the multiple polymerization rates and the average polymerization rate, and satisfying 0.8%/hr or less of the calculated standard deviation.

13. A non-transitory computer-readable medium including one or more instructions for:

acquiring a physical property value a derived from a functional group of a polymerizable reactive compound including an episulfide compound, and a polymerization catalyst;

heating the composition and maintaining the composition at a predetermined temperature, wherein the acquiring the physical property value a is conducted before the heating, acquiring a physical property value b derived from a remaining functional group after maintaining each of the plurality of predetermined temperatures for predetermined times;

calculating a remaining functional group ratio from the physical property value a and the physical property value b;

calculating a reaction rate coefficient from the remaining functional group ratio, based on a predetermined reaction rate equation stored in a storage unit;

back-calculating a plurality of polymerization temperatures at predetermined time intervals within a polymerization time based on the reaction rate equation, using the reaction rate coefficient, such that the following conditions are satisfied:

wherein the conditions are comprised of selecting and determining an average polymerization rate from a range of more than 0%/hr and 3.0%/hr or less in a range of 0% or more and 20% or less of a polymerization ratio, calculating multiple polymerization rates at predetermined time intervals within the time when the polymerization rate is range of 0% or more and 20% or less, and calculating a standard deviation by the positive square root of the variance of the multiple polymerization rates and the average polymerization rate, and satisfying 0.8%/hr or less of the calculated standard deviation; and carrying out a polymerization reaction according to the multiple polymerization rates at predetermined time intervals.

14. An optical material manufacturing device comprising:

a heating unit for heating a composition which includes a polymerizable reactive compound including an episulfide compound, and a polymerization catalyst;

the polymerization condition setting device according to claim 12; and a control unit for controlling the heating unit to heat the composition including the polymerizable reactive compound, which includes the episulfide compound, and the polymerization catalyst, based on polymerization temperature conditions obtained by the polymerization condition setting device.

15. The method for setting polymerization condition according to claim 1, wherein the reaction rate equation includes at least one of an nth-order reaction rate equation wherein n is 0 or more, a Prout-Tompkins rate equation, a Bawn rate equation, or a Leeson-Mattocks rate equation.

* * * * *